(12) United States Patent
Clawson

(10) Patent No.: US 8,712,020 B2
(45) Date of Patent: *Apr. 29, 2014

(54) PANDEMIC PROTOCOL FOR EMERGENCY DISPATCH

(76) Inventor: Jeffrey J. Clawson, Salt Lake City, UT (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/605,501

(22) Filed: Sep. 6, 2012

(65) Prior Publication Data

US 2014/0064462 A1    Mar. 6, 2014

(51) Int. Cl.
*H04M 11/04*    (2006.01)

(52) U.S. Cl.
USPC ............... 379/45; 379/38; 379/265.01; 705/2

(58) Field of Classification Search
USPC ...................................... 379/37, 45
See application file for complete search history.

(56) References Cited

U.S. PATENT DOCUMENTS

| | | |
|---|---|---|
| 3,799,147 A | 3/1974 | Adolph et al. |
| 4,130,881 A | 12/1978 | Haessler et al. |
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Lamb et al. |
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |

(Continued)

FOREIGN PATENT DOCUMENTS

| | | |
|---|---|---|
| GB | 2471960 | 1/2011 |
| JP | 2002-049693 | 2/2002 |

(Continued)

OTHER PUBLICATIONS

Radosevich, Lynda, "Network holds sway on life, death," Computerworld, v27 n21, May 24, 1993, 2 pgs.

(Continued)

*Primary Examiner* — Joseph J Nguyen
(74) *Attorney, Agent, or Firm* — John R. Thompson; Stoel Rives LLP

(57) ABSTRACT

Systems and methods are provided to guide an emergency dispatcher in responding to emergency calls involving a patient manifesting symptoms of a pandemic illness. The systems and methods may include an emergency dispatch protocol configured to facilitate uniform and consistent gathering of information concerning the emergency situation. The emergency medical dispatch protocol may include one or more dispatch protocols configured for particular emergency situations, such as to aid the dispatcher in processing calls relating to a pandemic illness (e.g., severe respiratory infection like influenza). The emergency dispatch protocol may present a pre-scripted interrogation, including preprogrammed inquiries for a dispatcher to ask the caller. The pre-scripted interrogation of the dispatch protocol facilitates uniform and consistent gathering of symptom information relating to a pandemic outbreak. The information may be received and stored and/or processed to determine a determinant value corresponding to an appropriate emergency dispatch response.

29 Claims, 14 Drawing Sheets

(56) References Cited

U.S. PATENT DOCUMENTS

| | | |
|---|---|---|
| 5,072,383 A | 12/1991 | Brimm et al. |
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |
| 5,193,855 A | 3/1993 | Shamos |
| 5,228,449 A | 7/1993 | Christ et al. |
| 5,253,164 A | 10/1993 | Holloway et al. |
| 5,255,187 A | 10/1993 | Sorensen |
| 5,291,399 A | 3/1994 | Chaco |
| 5,323,444 A | 6/1994 | Ertz et al. |
| 5,339,351 A | 8/1994 | Hoskinson et al. |
| 5,348,008 A | 9/1994 | Bornn et al. |
| 5,379,337 A | 1/1995 | Castillo et al. |
| 5,404,292 A | 4/1995 | Hendrickson |
| 5,410,471 A | 4/1995 | Alyfuku et al. |
| 5,423,061 A | 6/1995 | Fumarolo et al. |
| 5,438,996 A | 8/1995 | Kemper et al. |
| 5,441,047 A | 8/1995 | David et al. |
| 5,462,051 A | 10/1995 | Oka et al. |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,536,084 A | 7/1996 | Curtis et al. |
| 5,544,649 A | 8/1996 | David et al. |
| 5,554,031 A | 9/1996 | Moir et al. |
| 5,590,269 A | 12/1996 | Kruse et al. |
| 5,594,638 A | 1/1997 | Iliff |
| 5,594,786 A | 1/1997 | Chaco et al. |
| 5,596,994 A | 1/1997 | Bro |
| 5,630,125 A | 5/1997 | Zellweger |
| 5,636,873 A | 6/1997 | Sonsteby |
| 5,650,995 A | 7/1997 | Kent |
| 5,660,176 A | 8/1997 | Iliff |
| 5,675,372 A | 10/1997 | Aguayo, Jr. et al. |
| 5,682,419 A | 10/1997 | Grube et al. |
| 5,684,860 A | 11/1997 | Milani et al. |
| 5,689,229 A | 11/1997 | Chaco et al. |
| 5,719,918 A | 2/1998 | Serbetciouglu et al. |
| 5,722,418 A | 3/1998 | Bro |
| 5,724,983 A | 3/1998 | Selker et al. |
| 5,734,706 A | 3/1998 | Windsor et al. |
| 5,745,532 A | 4/1998 | Campana, Jr. |
| 5,748,907 A | 5/1998 | Crane |
| 5,754,960 A | 5/1998 | Downs et al. |
| 5,759,044 A | 6/1998 | Redmond |
| 5,761,278 A | 6/1998 | Pickett et al. |
| 5,761,493 A | 6/1998 | Blakeley et al. |
| 5,787,429 A | 7/1998 | Nikolin, Jr. |
| 5,805,670 A | 9/1998 | Pons et al. |
| 5,809,493 A | 9/1998 | Ahamed et al. |
| 5,822,544 A | 10/1998 | Chaco et al. |
| 5,823,948 A | 10/1998 | Ross, Jr. et al. |
| 5,826,077 A | 10/1998 | Blakeley et al. |
| 5,832,187 A | 11/1998 | Pedersen et al. |
| 5,842,173 A | 11/1998 | Strum et al. |
| 5,844,817 A | 12/1998 | Lobley et al. |
| 5,850,611 A | 12/1998 | Krebs |
| 5,857,966 A | 1/1999 | Clawson |
| 5,901,214 A | 5/1999 | Shaffer et al. |
| 5,902,234 A | 5/1999 | Webb |
| 5,910,987 A | 6/1999 | Ginter et al. |
| 5,912,818 A | 6/1999 | McGrady et al. |
| 5,915,019 A | 6/1999 | Ginter et al. |
| 5,926,526 A | 7/1999 | Rapaport et al. |
| 5,933,780 A | 8/1999 | Connor et al. |
| 5,961,446 A | 10/1999 | Beller et al. |
| 5,962,891 A | 10/1999 | Arai |
| 5,964,700 A | 10/1999 | Tallman et al. |
| 5,986,543 A | 11/1999 | Johnson |
| 5,989,187 A | 11/1999 | Clawson |
| 5,991,730 A | 11/1999 | Lubin et al. |
| 5,991,751 A | 11/1999 | Rivette et al. |
| 6,004,266 A | 12/1999 | Clawson |
| 6,010,451 A | 1/2000 | Clawson |
| 6,022,315 A | 2/2000 | Iliff |
| 6,035,187 A | 3/2000 | Franza |
| 6,040,770 A | 3/2000 | Britton |
| 6,052,574 A | 4/2000 | Smith, Jr. |
| 6,053,864 A | 4/2000 | Clawson |
| 6,058,179 A | 5/2000 | Shaffer et al. |
| 6,074,345 A | 6/2000 | van Oostrom et al. |
| 6,076,065 A | 6/2000 | Clawson |
| 6,078,894 A | 6/2000 | Clawson et al. |
| 6,106,459 A | 8/2000 | Clawson |
| 6,112,083 A | 8/2000 | Sweet et al. |
| 6,115,646 A | 9/2000 | Fiszman et al. |
| 6,117,073 A | 9/2000 | Jones et al. |
| 6,118,866 A | 9/2000 | Shtivelman |
| 6,127,975 A | 10/2000 | Maloney |
| 6,134,105 A | 10/2000 | Lueker |
| 6,292,542 B1 | 9/2001 | Bilder |
| 6,370,234 B1 | 4/2002 | Kroll |
| 6,535,121 B2 | 3/2003 | Matheny |
| 6,594,634 B1 | 7/2003 | Hampton et al. |
| 6,607,481 B1 | 8/2003 | Clawson |
| 6,610,012 B2 | 8/2003 | Mault |
| 6,696,956 B1 | 2/2004 | Uchida et al. |
| 6,879,819 B2 | 4/2005 | Brooks |
| 6,901,397 B1 | 5/2005 | Moldenhauer et al. |
| 6,931,112 B1 | 8/2005 | McFarland et al. |
| 6,968,375 B1 | 11/2005 | Brown |
| 7,106,835 B2 | 9/2006 | Saalsaa |
| 7,194,395 B2 | 3/2007 | Genovese |
| 7,289,944 B1 | 10/2007 | Genovese |
| 7,428,301 B1 | 9/2008 | Clawson |
| 7,436,937 B2 | 10/2008 | Clawson |
| 7,645,234 B2 | 1/2010 | Clawson |
| 7,703,020 B2 | 4/2010 | Bhattaru |
| 7,783,586 B2 | 8/2010 | Friedlander et al. |
| 7,978,826 B2 | 7/2011 | Salafia et al. |
| 8,294,570 B2 | 10/2012 | Clawson |
| 8,335,298 B2 | 12/2012 | Clawson |
| 2002/0004729 A1 | 1/2002 | Zak et al. |
| 2002/0106059 A1 | 8/2002 | Kroll et al. |
| 2003/0028536 A1 | 2/2003 | Singh et al. |
| 2003/0050538 A1 | 3/2003 | Naghavi et al. |
| 2003/0187615 A1 | 10/2003 | Epler |
| 2003/0195394 A1 | 10/2003 | Saalsaa |
| 2003/0212575 A1 | 11/2003 | Saalsaa et al. |
| 2005/0015115 A1 | 1/2005 | Sullivan et al. |
| 2006/0059423 A1 | 3/2006 | Lehmann et al. |
| 2006/0122520 A1 | 6/2006 | Banet et al. |
| 2006/0167346 A1 | 7/2006 | Sarel |
| 2006/0173500 A1 | 8/2006 | Walker et al. |
| 2006/0178908 A1 | 8/2006 | Rappaport |
| 2006/0212315 A1 | 9/2006 | Wiggins |
| 2006/0225213 A1 | 10/2006 | Tomcany |
| 2007/0055559 A1 | 3/2007 | Clawson |
| 2007/0112275 A1 | 5/2007 | Cooke et al. |
| 2007/0116189 A1 | 5/2007 | Clawson |
| 2007/0201664 A1 | 8/2007 | Salafia et al. |
| 2008/0208801 A1 | 8/2008 | Friedlander et al. |
| 2008/0310600 A1 | 12/2008 | Clawson |
| 2009/0168975 A1 | 7/2009 | Clawson |
| 2009/0191529 A1 | 7/2009 | Mozingo et al. |
| 2010/0004710 A1 | 1/2010 | Kellum |
| 2010/0121156 A1 | 5/2010 | Yoo |
| 2010/0152800 A1 | 6/2010 | Walker et al. |
| 2010/0198755 A1 | 8/2010 | Soll et al. |
| 2010/0257250 A1 | 10/2010 | Salafia et al. |
| 2011/0064204 A1 | 3/2011 | Clawson |
| 2011/0066002 A1 | 3/2011 | Clawson |
| 2011/0099031 A1 | 4/2011 | Nair |
| 2011/0205052 A1 | 8/2011 | Clawson |
| 2011/0215930 A1 | 9/2011 | Lee |
| 2012/0183128 A1 | 7/2012 | Clawson |
| 2012/0207286 A1 | 8/2012 | Clawson |
| 2012/0210271 A1 | 8/2012 | Clawson |

(56) References Cited

U.S. PATENT DOCUMENTS

FOREIGN PATENT DOCUMENTS

| JP | 2003-109162 A | 4/2003 |
|---|---|---|
| JP | 2003-187003 A | 7/2003 |
| JP | 2003-256963 A | 12/2003 |
| JP | 2010-033201 A | 12/2010 |
| KR | 10-2005-0085778 | 8/2005 |
| KR | 10-2006-0084866 | 7/2006 |
| KR | 2007-0043337 A | 4/2007 |
| KR | 10-2008-0004125 | 1/2008 |
| WO | WO2004/030259 | 4/2004 |
| WO | WO2006/015229 A2 | 2/2006 |
| WO | WO2008/156876 A1 | 12/2008 |
| WO | WO 2011031383 | 3/2011 |

OTHER PUBLICATIONS

Harris, Roger, "Updated 911 Phone System Top Concern of Residents," Business First-Louisville, v9 n19 s1, Dec. 1992, 3 pgs.
"Geac Completes Software Install," Wireless Week, Nov. 18, 1996, 3 pgs.
"Dictaphone introduces Windows-based Computer-Aided Dispatch (CAD) system," Business Wire, Apr. 23, 1996, 2 pgs. (in commercial use in 1995).
Holroyd, Brian, et al., "Medical Control; Quality Assurance in Prehospital Care," JAMA, The Journal of American Medical Association, v256, n8, Aug. 1986, p. 1027-1031.
CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 mailed Dec. 31, 2003, 8 pgs.
Office Action Summary from USPTO for U.S. Appl. No. 10/255,901 mailed Oct. 13, 2004, 8 pgs.
Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
Notification of Transmittal of the International Search Report (2 pgs.) for PCT/US2009/040909, International Search Report, (2 pgs.), and Written Opinion (8 pgs.) mailed from International Searching Authority on Jun. 10, 2009.
International Search Report and Written Opinion for PCT/US09/48577, International filed Jun. 25, 2009, mailed from ISA Aug. 7, 2009, 9 pgs.
International Search Report and Written Opinion mailed Jan. 19, 2011 in PCT Application No. PCT/US2010/043308, filed Jul. 27, 2010.
International Search Report and Written Opinion mailed Jan. 19, 2011 in PCT Application No. PCT/US2010/043311, filed Jul. 27, 2010.
Office Action Summary from USPTO for U.S. Appl. No. 12/396,201 mailed Mar. 8, 2011, 23 pgs.
International Search Report and Written Opinion PCT/US2010/050402, filed on Sep. 27, 2010, and mailed from ISA on Apr. 27, 2011, 9 pgs.
Office Action Summary from USPTO for U.S. Appl. No. 12/268,963 mailed Jul. 29, 2011, 18 pgs.
International Preliminary Report of Patentability for PCT/US2009/048577 filed on Jun. 25, 2009 mailed Oct. 27, 2011, 7 pgs.
International Search Report and Written Opinion for PCT/US2011/042543 filed on Jun. 30, 2011, and mailed from ISA on Feb. 9, 2012, 11 pgs.
International Search Report and Written Opinion for PCT/US2011/042582 filed on Jun. 30, 2011, and mailed from ISA on Feb. 9, 2012, 8 pgs.
International Preliminary Report of Patentability for PCT/US2010/043308 filed on Jul. 27, 2010 mailed Mar. 22, 2012, 6 pgs.
International Preliminary Report of Patentability for PCT/US2010/043311 filed on Jul. 27, 2010 mailed Mar. 29, 2012, 6 pgs.
Office Action Summary from USPTO for U.S. Appl. No. 12/558,045 mailed Mar. 22, 2012, 9 pgs.
Office Action Summary from USPTO for U.S. Appl. No. 12/558,808 mailed Apr. 23, 2012, 9 pgs.
Office Action Summary from USPTO for U.S. Appl. No. 12/422,561 mailed Jul. 3, 2012, 21 pgs.
International Search Report and Written Opinion for PCT/US2012/021867 filed on Jan. 19, 2012, and mailed from ISA on Aug. 30, 2012, 8 pgs.

(56) References Cited

OTHER PUBLICATIONS

Office Action Summary from USPTO for U.S. Appl. No. 13/354,116 mailed Jan. 22, 2013, 9 pgs.
Office Action Summary from USPTO for U.S. Appl. No. 12/422,561 mailed Feb. 1, 2013, 26 pgs.
Notice of Allowance from USPTO for U.S. Appl. No. 13/026,055 mailed Jan. 24, 2013.
Notice of Allowance from USPTO for U.S. Appl. No. 10/255,901 mailed Feb. 20, 2013.
Nordberg, Marie, "Dispatch Disasters," Emergency Medicine, Aug. 1995.
International Search Report and Written Opinion for PCT/US2013/055537 filed on Aug. 19, 2013 and mailed from ISA on Nov. 22, 2013.
Notice of Allowance from USPTO for U.S. Appl. No. 13/026,043 mailed Jan. 13, 2014.
Nor, A. Mohd, et al., "Agreement Between Ambulance Paramedic- and Physician-Recorded Neurological Signs With Face Arm Speech Test (FAST) in Acute Stroke Patients", http://stroke.ahajournals.org/content/3516/1355, Apr. 29, 2004, visited Nov. 17, 2013, 3 pgs.
Liferidge, Aisha T., et al., "Ability of Laypersons to Use the Cincinnati Prehospital Stroke Scale", Prehospital Emergency Care, Elsevier, vol. 8, No. 4, Oct. 1, 2004, pp. 384-387.
Office Action Summary from USPTO for U.S. Appl. No. 13/026,043 mailed Oct. 10, 2013.
Notice of Allowance from USPTO for U.S. Appl. No. 13/354,116 mailed Jun. 7, 2013.
International Preliminary Report of Patentability for PCT/US2011/042543 filed on Jun. 30, 2011 mailed Aug. 22, 2013, 7 pgs.
International Preliminary Report of Patentability for PCT/US2011/042582 filed on Jun. 30, 2011 mailed Aug. 22, 2013, 5 pgs.

PANDEMIC PROTOCOL FOR EMERGENCY DISPATCH

COPYRIGHT NOTICE

© 2012 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

TECHNICAL FIELD

The present disclosure relates to computer systems and methods for providing medical protocol interrogation, instruction, and emergency dispatch. More specifically, the disclosure is directed to computer-implemented protocols to enable a dispatcher to process emergency calls in an accurate, consistent, and systematic manner by guiding the dispatcher during interrogation and instruction of an emergency caller.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Figure 1:
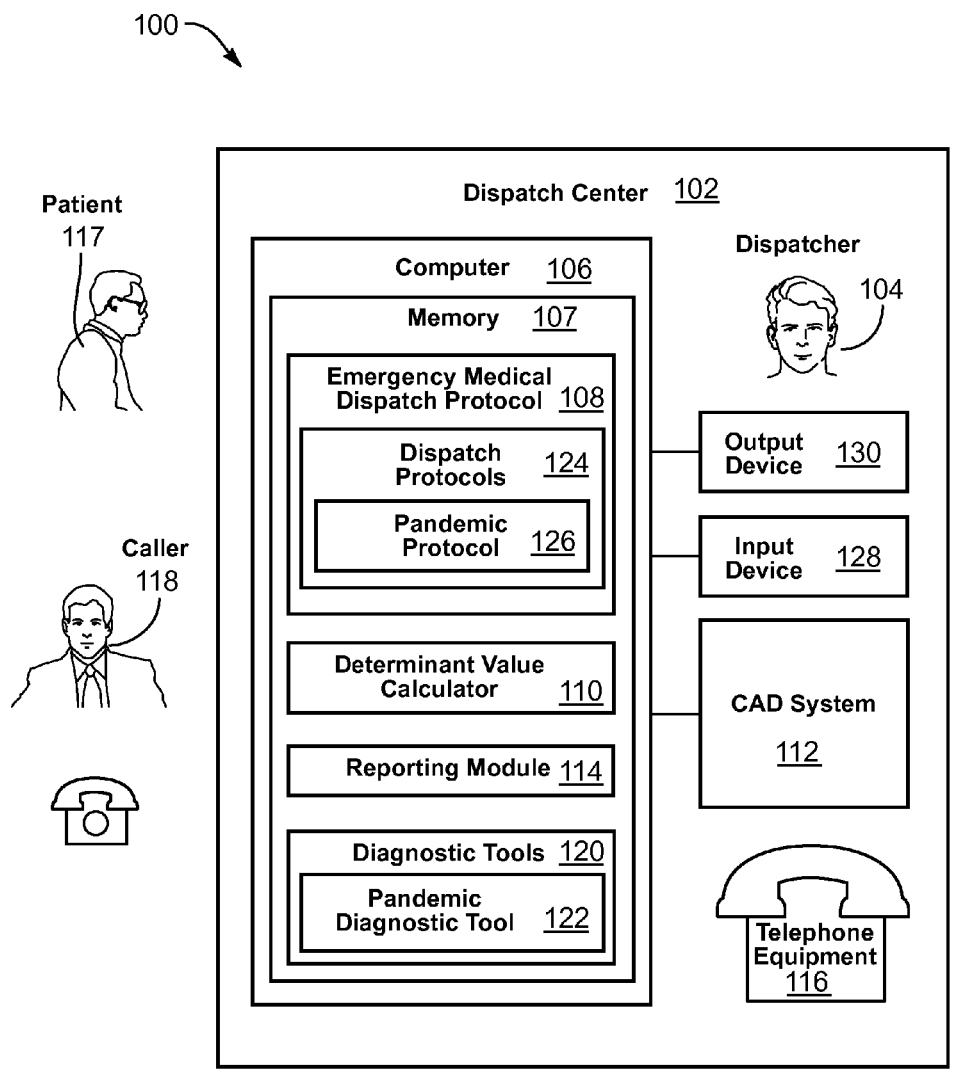
FIG. 1 is a block diagram of an emergency medical dispatch system, according to one embodiment.

A pandemic outbreak (or simply a pandemic) involves an infectious disease that is prevalent over a widespread geographic area and that affects a large proportion of a population (i.e., the public) in that geographic area. An epidemic may be considered a pandemic on a smaller scale. A pandemic is significant and concerning because of the potential that all the individuals of the population may be at risk of suffering serious illness or even death. A pandemic can cause fear and apprehension, and can close schools, places of business, and other public places. A pandemic can also potentially disrupt economic activity and development, thereby introducing other far-reaching effects.

A pandemic is also concerning because it can place sudden and intense demands on healthcare systems. The rampant nature by which a pandemic can spread may require a large proportion of available healthcare resources and providers to treat the victims of the illness. Especially worrisome is that the infectious nature of a pandemic illness puts at risk the healthcare providers who are trained to treat the illness and stop it from spreading. In other words, a pandemic can be dangerous for the public at large because of the demands on and risks posed to the public's defense mechanism against the illness, namely the healthcare systems and healthcare providers (collectively "healthcare providers").

While public health officials agree that a pandemic is a concerning and significant situation, not all agree on the criteria that characterize a pandemic. The size of a geographic region and the proportion of a population of that region that must be affected to constitute a pandemic are criteria that are inherently ambiguous, subjective, and relative, and consequently are constantly subject to debate. Views diverge as to the appropriate standard for initially categorizing an outbreak of an illness as an epidemic, and the appropriate standard for categorizing when an outbreak then becomes a pandemic. Various local, national, and international health officials and organizations have established standards of criteria to define a pandemic (and an epidemic), and understandably not all are alike. Despite the diverging standards, a person of ordinary skill will appreciate that an infectious disease posing a threat to spread among the public, whether of epidemic or pandemic proportions, and whether unofficially or officially categorized as such, creates a situation with issues and concerns analogous to those of a clearly severe pandemic. Accordingly, as used herein, the term pandemic can encompass all situations relating to an infectious disease spreading, or posing a threat to spread, among the public.

The infectious nature of a pandemic, the threat to the public at large, and the risks posed to healthcare providers may suggest that an emergency response tailored to the particular pandemic illness would be beneficial. For example, there may be reason for heightened precautions and procedures, reason to monitor the location of the illness and track its progress, and reason to isolate or even quarantine cases of the illness. Unfortunately, existing methods and systems offer little to facilitate providing an appropriate emergency response to an emergency situation involving a pandemic illness. More particularly, present systems and methods do not facilitate providing accurate, consistent, and systematic processing of emergency calls involving a pandemic illness.

Emergency dispatchers are often an early interface to healthcare systems. In their role receiving emergency calls, a dispatcher is in a unique position to potentially be the first to identify and or report a potential case of a pandemic illness. Unfortunately, often emergency dispatchers are inexperienced and unskilled, largely due to a high turnover rate among emergency dispatchers. An automated emergency dispatch system, potentially implemented on a computer, can aid an unskilled and inexperienced dispatcher in prioritizing emergency calls received and processing the calls to generate an appropriate emergency dispatch response. Regardless of the experience or skill level of the dispatcher, the automated emergency dispatch systems can enable a consistent and predictable emergency dispatch response, despite the diverse aspects of emergency situations, including inter alia signs, symptoms, conditions, and circumstances, that may be reported from one call to the next.

Although an automated emergency dispatch system can enable receiving and processing of widely divergent aspects of emergency situations, these systems may not be well suited for processing particular types of unique situations. An emergency situation relating to a pandemic illness, or involving symptoms of such illness, may require considering the situation as it occurs within the context of a larger public emergency. An emergency situation involving the pandemic illness should be handled on an individual basis, but also with the larger community in mind and with an objective of tracking and even containing the illness. Precautions must be taken to ensure that the pandemic illness is properly tracked and handled. As such, the emergency situations involving a pandemic illness may benefit from particular and more detailed instructions. Additional interrogation, instructions, and/or alternative emergency dispatch procedures or protocols may facilitate tracking and/or containing the pandemic illness.

Existing automated emergency dispatch systems are not equipped to assist or enable a dispatcher to process an emergency call involving a pandemic illness. A dispatcher with little or no medical training or experience likely cannot compensate for the shortcomings of an automated emergency dispatch system. Inexperienced and/or unskilled dispatchers are generally unable to properly explore situations and/or aspects or diagnose medical conditions, let alone instruct a caller to do so. Even highly skilled and experienced dispatchers may have little skill or experience with handling pandemic situations, simply because pandemic emergencies are relatively rare. Accordingly, the present disclosure provides a method and system for processing of emergency calls involving a pandemic illness in a rapid, consistent, and predictable manner.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or computer-readable storage medium. A software module may, for instance, comprise one or more physical or logical blocks of computer instructions, which may be organized as a routine, program, object, component, data structure, etc. that performs one or more tasks or implements particular abstract data types.

In certain embodiments, a particular software module may comprise disparate instructions stored in different locations of a memory storage device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network.

In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools.

An emergency dispatch system as disclosed herein may be computer-implemented in whole or in part on a digital computer. The digital computer includes a processor performing the required computations. The computer further includes a memory in electronic communication with the processor to store a computer operating system. The computer operating systems may include, but are not limited to, MS-DOS, Windows, Linux, Unix, AIX, CLIX, QNX, OS/2, and Apple. Alternatively, it is expected that future embodiments will be adapted to execute on other future operating systems.

The memory may also store application programs including a Computer Aided Dispatch (CAD) program, an automated emergency dispatch protocol, and a user interface program. The memory may also include data storage. The computer may further include an output device, such as a display unit, for viewing the displayed instructions and inquiries and a user input device for inputting response data.

FIG. 1 is an emergency medical dispatch system 100, according to one embodiment. At a dispatch center 102, a dispatcher 104 may operate a computer 106. The computer 106 may include a memory 107 to store protocols, modules, tools, data, etc. The computer 106 may be configured to follow an emergency medical dispatch protocol 108 to enable the dispatcher 104 to rapidly and consistently address a medical emergency of a patient 117 as reported by a caller 118. The emergency medical dispatch protocol 108 may include a logic tree, inquiries or questions, possible responses from a caller 118 to the inquiries, and instructions to the caller 118. The responses may route to subsequent inquiries and/or instructions to the caller 118. The emergency medical dispatch protocol 108 may also include dispatch protocols 124 for guiding the dispatcher 104 in processing emergency calls involving specific situations and/or patient conditions. The dispatch protocols 124 may similarly include a logic tree, inquiries or questions, possible responses from a caller 118 to the inquiries, and instructions for the caller 118. The dispatch protocols 124 may include a pandemic protocol 126 for rapid, consistent, and predictable processing of emergency calls involving a pandemic illness.

The responses of the caller 118 are processed according to predetermined logic of the logic tree of the emergency medical dispatch protocol 108. The predetermined logic may enable the emergency medical dispatch system 100 to provide to the dispatcher 104 information concerning the correct emergency medical dispatch response (e.g., by trained emergency responders). The predetermined logic may also enable the emergency medical dispatch system 100 to provide to the dispatcher 104 appropriate doctor-approved post-dispatch instructions for relay to the caller 118 before professional help arrives at the scene. The predetermine logic may also enable the emergency medical dispatch system 100 to aid the dispatcher in determining an appropriate priority of the emergency call, including but not limited to a priority of the emergency call relative to other emergency calls and the level of emergency response provided for the emergency.

Although an emergency medical dispatch system 100 and an emergency medical dispatch protocol 108 are disclosed and described herein, a person of ordinary skill can appreciate that other emergency dispatch systems and protocols are contemplated, including but not limited to emergency fire dispatch systems and protocols and emergency police dispatch systems and protocols. Exemplary embodiments of emergency dispatch systems and protocols are disclosed in U.S. Pat. Nos. 5,857,966, 5,989,187, 6,004,266, 6,010,451, 6,053,864, 6,076,065, 6,078,894, 6,106,459, 6,607,481, 7,106,835, 7,428,301, and 7,436,937, which are hereby incorporated herein by reference.

The computer 106 operates a determinant value calculator 110 to calculate a determinant value from the responses of the caller 118 to protocol questions. The determinant value may be selected from a group of pre-established determinant values, such that the emergency responders are familiar with the determinant values and understand the meaning of each and what would be a corresponding emergency response. For example, the determinant values may range from D-1 for generally very serious emergencies to A-2 for generally less serious emergencies. The determinant value may provide a categorization code of the type and level of the incident.

Many calls for medical services are not true medical emergencies, so it is important to prioritize the calls in several ways. First, calls that are true emergencies should be dispatched first. Second, if an agency has units with different capabilities, the emergencies involving more severe medical problems can be sent units that are more skilled and advanced. And finally, if lights-and-siren are not needed from a medical standpoint, they should not be used, thereby increasing the safety of all those on the road and in the emergency response vehicles. The computer 106 presents the determinant value to generate an appropriate emergency dispatch response and/or establish the priority of the emergency call. The response may include dispatching professional emergency responders to the scene of the emergency. Because the questions asked and the recommendations that are made deal directly with life and death decisions, the protocols used shall have passed through a rigorous medical review by a panel of doctors and EMS public safety experts who specialize in emergency medicine.

The determinant value may be provided to a Computer Aided Dispatch (CAD) system 112, which is a tool that a dispatcher 104 may use to track and allocate emergency response resources for processing emergency calls. The CAD may manage dispatcher tools for processing emergency calls, including but not limited to the emergency dispatch protocol 108, communication resources (e.g., radio system, alpha pager), mapping tools (e.g., global positioning system (GPS) technology), and vehicle location systems (e.g., automatic vehicle location (AVL)). The CAD system 112 may operate in whole or in part on a separate computer in communication with the computer 106. In another embodiment, the CAD system 112 operates on the computer 106. The primary information used by the CAD system 112 is location information of both the incident and units, unit availability and the type of incident. The CAD system 112 may use third party solutions, such as E-911, vehicle location transponders and mobile data terminals (MDT's) for automating the location and availability tasks. The CAD system may also use an emergency dispatch protocol 108 to facilitate structured call taking for incident interrogation, as previously described.

While many medical calls are not true emergencies, all situations can benefit from medical evaluation and instruction. Prior to the arrival of professional help on-scene, the emergency medical dispatch protocol 108 may provide the dispatcher 104 with instructions for the caller 118 that are appropriate to the type of call, whether the call relates to a patient 117 with minor lacerations or a patient 117 who is not breathing. These instructions may help expedite the work of emergency responders.

The computer 106 may also include a reporting module 114 to statistically measure the performance of individual staff and overall performance of the dispatch center 102. These statistics may include compliance rates, call processing statistics, and peer measurements.

The computer 106 may further comprise an input device 128, such as a keyboard, mouse, laser pointer, or other input device, and also an output device 130, such as a display monitor. The input device 128 receives input from a user (generally a dispatcher) and provides it to the emergency medical dispatch system 100. The input may be provided to the computer 106, the emergency protocol 108, the diagnostic tool 120, and/or the CAD system 112. An output device 130 receives output from the emergency medical dispatch system 100 and displays or otherwise provides the output to the user. In another embodiment, the input device 128 and output device 130 are provided by the CAD system 112.

The dispatch center 102 includes a communication device 116 (e.g., telephone equipment) to answer emergency calls. A call into the dispatch center 102 from a caller 118 initiates creation of a medical call incident. The dispatcher 104 identifies the call as requiring an emergency medical dispatch, and the emergency medical dispatch protocol 108 is accessed. The protocol 108, including the dispatch protocols 124, may provide questions and/or instructions that are expertly drafted to assist a novice caller 118 in diagnosing a condition of a patient 117. The protocol 108 may also provide expertly drafted first aid instructions to assist a patient 117 prior to the arrival of trained emergency responders. Some of the instructions may be vocally relayed by the dispatcher 104 to the caller 118 over the communication device 116.

Some protocol questions may be readily answerable by the caller 118, whereas others may be more difficult to answer. Certain diagnostic inquiries may be difficult for the untrained caller to determine or may be difficult to answer under the stress of an emergency situation. Accordingly, in addition to instructions, the emergency medical dispatch system 100 may provide one or more computer-implemented diagnostic tools 120. The diagnostic tools 120 may greatly improve information collection and intervention for emergency medical response situations and aid in saving lives.

A diagnostic tool 120 may aid the dispatcher 104 and/or the caller 118 (via instructions from the dispatcher 104) in diagnosing a condition of a patient 117. A diagnostic tool 120 may also be an interventional tool, providing instructions that direct a caller 118 to intervene, or take action, to treat a patient 117, or otherwise change the circumstances or conditions of an emergency situation. For sake of clarity, diagnostic tools and interventional tools are both referred to herein generally as diagnostic tools. Accordingly, a diagnostic tool 120, as referred to herein, may provide diagnostic instructions, interventional instructions, or both diagnostic and interventional instructions. Whether a diagnostic tool 120 provides merely diagnostic instructions, merely interventional instructions, or both diagnostic and interventional instructions, the diagnostic tool provides consistent and reliable instruction, information gathering, and/or timing for a particular emergency situation.

The diagnostic tools 120 are computer implemented software modules that enable a dispatcher 104 to provide consistent, expert advice to assist a caller with regards to a particular aspect of an emergency situation, such as determining a vital sign. One benefit of the diagnostic tools 120 is the computer aided timing of techniques to determine the vital signs. In highly stressful conditions, the diagnostic tools 120 provide a necessary resource to reading critical signs. The diagnostic tools 120 may be stored in the memory of the computer 106 and initiated and executed as required. The diagnostic tools 120 may be embodied as computer executable software applications and associated data.

The protocol 108, including the dispatch protocols 124, also may call on one or more diagnostic tools 120 to assist with an inquiry and may route to the appropriate diagnostic tool 120 when needed. When directed according to the protocol, the emergency medical dispatch protocol 108 may automatically, i.e., without dispatcher intervention, initiate the appropriate diagnostic tool 120. This may occur when the emergency medical dispatch protocol 108 arrives at a diagnosis step in the logic tree. The emergency medical dispatch system 100 may also allow the dispatcher 104 the option to call upon a diagnostic tool 120 as desired. Icons may be displayed in a tool bar, or other convenient location on a user interface to allow the dispatcher 104 to initiate a corresponding diagnostic tool 120. One particular diagnostic tool 120 discussed herein may be a pandemic diagnostic tool 122, an example of which is disclosed in U.S. patent application Ser. No. 12/558,808, which is hereby incorporated by reference herein in its entirety.

The pandemic diagnostic tool 122 may be configured as a surveillance tool to collect information in order to identify patterns, trends, and geographical clusters of symptoms of a particular pandemic illness. The pandemic diagnostic tool 122 is configured to facilitate consistent, uniform collection of information, such that the information is gathered in substantially the same manner and seeking substantially the same set of information for all cases, regardless of the skill or experience of the dispatcher. The gathered symptom information is uniform and quantifiable and can be appropriately measured or compared against other data gathered in a similar manner.

The symptom information gathered by the pandemic diagnostic tool 122 can be used by local public health authorities to attempt to determine if pandemic outbreak may be occurring in a particular region. The symptom information gathered by the pandemic diagnostic tool 122 can be stored for tracking purposes and also communicated to emergency response agencies to alert the emergency responders of the potential for contact with the particular pandemic illness, so that they can take any potential precautionary measures. The symptom information can also be communicated to the emergency medical dispatch protocol 108, including the dispatch protocols 124, for use in determining appropriate questions and/or instructions to provide to the dispatcher 104.

The pandemic diagnostic tool 122 may be launched from within, or at least in conjunction with, the progression of the emergency medical dispatch protocol 108 and dispatch protocols 124, including the pandemic protocol 126, to enhance and supplement emergency call processing facilitated by the emergency medical dispatch protocol. The pandemic diagnostic tool 122 may be launched automatically by the emergency medical dispatch protocol 108, or launched manually by a dispatcher 104.

Figure 2:
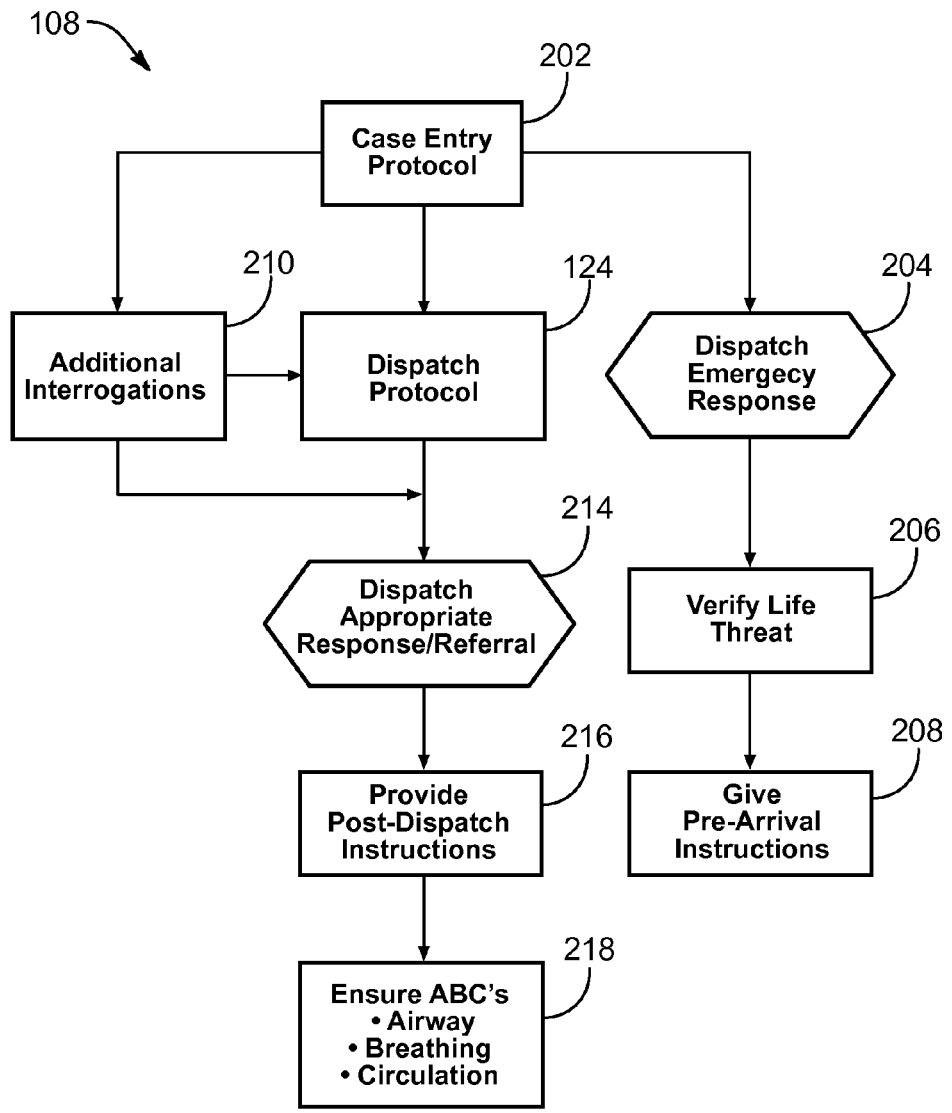
FIG. 2 is a flow diagram of an emergency medical dispatch protocol of an emergency medical dispatch system, according to one embodiment.

FIG. 2 is a flow diagram of an emergency medical dispatch protocol 108 of an emergency medical dispatch system, according to one embodiment. The protocol 108 may begin with a case entry protocol 202 that guides the dispatcher in gathering initial information. One aim of the case entry protocol 202 is to obtain sufficient information from the caller to permit identification of the patient's chief complaint. Also, the case entry protocol 108 may be considered a primary interrogation because all calls may be processed through the case entry protocol 202 to gather initial patient information and symptom information. The information received through the case entry protocol 202 may include a description of the problem (e.g., the patient's complaint), the patient's age, the status of the patient's breathing, and the status of the patient's consciousness. This information is also referred to in the field of art as "the four commandments of emergency medical dispatching."

If the caller relays information to the dispatcher that the patient is unconscious and not breathing (or unconscious and breathing is uncertain, or conscious but not breathing where the failure to breathe has been verified), for whatever reason, an emergency response is dispatched 204 immediately, before continuing with any further interrogation or instructions. The dispatched emergency response 204 may be a maximum emergency response, which may include such resources as emergency medical technicians, ambulances, paramedics, and other appropriate healthcare providers. The life threat 206 is verified and pre-arrival instructions are given 208. The pre-arrival instructions can be tailored to the specific situation and/or condition of the patient, and may include treatment sequence scripts covering, inter alia, cardiac arrest, choking, and childbirth. For example, the treatment sequence scripts may enable the dispatcher to guide the caller in CPR, the Heimlich Maneuver, or emergency childbirth procedures. Typically, the result of properly conveyed (by the dispatcher) and executed (by the caller) instructions is a more viable patient at the time the emergency responders arrive.

If the dispatcher receives information from the caller to confirm the patient is breathing, but the dispatcher lacks sufficient information to proceed directly to a dispatch protocol 124, the emergency medical dispatch protocol 108 may shunt to additional inquiries 210 designed to guide the dispatcher to gather information from the caller to enable the dispatcher to ascertain the patient's chief complaint. If the patient's chief complaint is determined, the emergency medical dispatch protocol 108 may shunt to the appropriate dispatch protocol 124 for dealing with that chief complaint.

The dispatch protocol 124 may guide the dispatcher through a secondary interrogation focusing on the chief complaint. The dispatch protocol 124 may present a pre-scripted interrogation to enable a more orderly and detailed understanding of the patient so that the pre-hospital care provided by the emergency responders is appropriate for the severity of the patient's condition. The pre-scripted interrogation may include preprogrammed inquiries focused on gathering information relating to the chief complaint. The preprogrammed inquiries provided by the dispatch protocol 124 may be termed "Key Questions" for the particular situation or condition of the patient's chief complaint. The preprogrammed inquiries presented may depend on caller responses. Dispatch protocols 124, in general, are discussed in greater detail below with reference to FIG. 4. The heart of the instant disclosure is the dispatch protocol 124 for processing an emergency call involving a pandemic illness. The pandemic protocol will be discussed in greater detail below with reference to FIGS. 5A-5B, and 6A-6F.

During the dispatch protocol 124, the dispatcher and/or the emergency medical dispatch protocol 108 will gather, inter alia, signs, symptoms, conditions, and circumstances of the emergency situation and the patient's condition, discovered through interrogation, and may dispatch 214 an appropriate emergency dispatch response. The dispatch protocol 124 facilitates uniform and consistent gathering of information relating to the emergency and dispatching of an appropriate emergency dispatch response. The appropriate emergency dispatch response may be determined through a system of assigning determinant values as the protocol progresses (i.e., traverses) through a logic tree. The determinant values may range, for example, from D-1 for generally very serious emergencies to A-2 for generally less serious emergencies. When a determinant value is identified in one of the four levels (Alpha—A, Bravo—B, Charlie—C, and Delta—D) the response configuration (e.g., the emergency vehicles involved and the mode of response) is dispatched 214 as indicated by the dispatch protocol. If the protocol determines that the call does not constitute an emergency, a referral to another healthcare provider may be provided instead of dispatching an emergency dispatch response.

After the appropriate emergency dispatch response has been sent (e.g., emergency medical responders), the dispatcher may remain on the telephone with the caller to provide post-dispatch instructions 216 regarding what to do, and what not to do, prior to the arrival of the emergency responders. The post-dispatch instructions 216 help to prepare the patient for, and to expedite, the emergency responders' work at the scene. Post-dispatch instructions may include such instructions as "collect the patient's medications," "write down the name of the family doctor," and "put away pets," "if there is a defibrillator (AED) available, send someone to get it now in case we need it later," "stay on the line and I'll tell you exactly what to do next," and the like.

The caller may also be instructed to ensure 218 that the patient has an open airway, is breathing, and is given nothing to eat or drink before emergency responders arrive. If necessary, the caller may also be instructed how to treat for shock. The instructions may be provided with reference to a protocol for Airway, Breathing, and Circulation (the "ABC's"). The caller may also be advised to "call back if the patient's condition worsens for further instructions."

Figure 3:
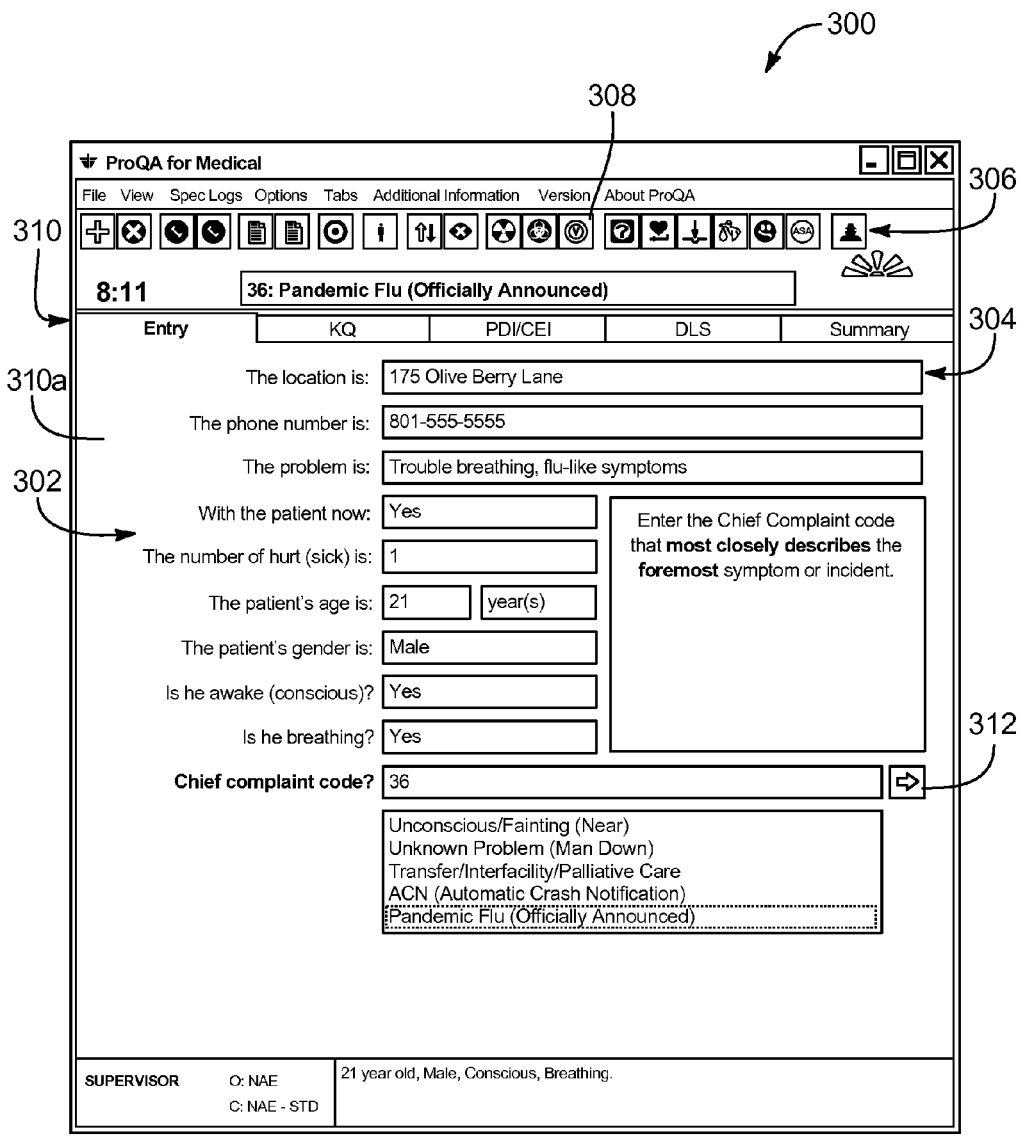
FIG. 3 is a user interface of an emergency medical dispatch system, according to one embodiment.

FIG. 3 is a user interface 300 of an emergency medical dispatch system, according to one embodiment. The emergency medical dispatch system user interface 300 allows a dispatcher to interface with the emergency medical dispatch protocol. The illustrated user interface 300 is shown traversing a case entry protocol 202 of the emergency medical dispatch protocol 108 (described above with reference to FIG. 2). The emergency medical dispatch protocol may present inquiries 302 (or questions) via the emergency medical dispatch system user interface 300. The inquiries 302 are provided for the dispatcher to relay to the caller to gather information regarding the medical emergency of the patient. The dispatcher and/or the emergency medical dispatch system may gather the information in the form of caller responses to the inquiries 302. The dispatcher may input the responses of the caller to the inquiries into response fields 304 provided by the user interface 300. The response fields 304 may include, for example, any of a number of appropriate input field types, including but not limited to text fields, text boxes, menus, drop down menus, drop-down selection boxes, lists, buttons, check boxes, and radio buttons. The response fields 304 may correspond to information indicative of one or more responses of the caller to the inquiries 302.

The caller responses are relayed from the caller to the dispatcher, typically over the telephone. Information from the caller responses may be input into the system by the dispatcher and may be used by the emergency medical dispatch protocol to determine subsequent inquiries 302 and instructions to present to the dispatcher. The caller response information may indicate the caller's observations of signs and symptoms of the patient's medical condition. The emergency medical dispatch system may use the caller response information to generate an emergency medical dispatch response by trained emergency responders. The information gathered from the caller responses may be used by the determinant value calculator to calculate a determinant value that can be communicated to the emergency responders. Additional details relating to emergency medical dispatch protocols and user interfaces to interact with the same can be found in the earlier referenced U.S. patents. In addition, similar concepts are discussed below in relation to a dispatch protocol, and in particular a pandemic protocol, with reference to FIGS. 4, 5A-5B, and 6A-6F.

The user interface 300 may further comprise tabs 310 to aid in organizing and/or compartmentalizing various aspects of processing a call. The tabs 310 may include a tab 310*a* for presenting a case entry protocol portion of an emergency medical dispatch protocol (e.g., "Entry" tab). Other tabs may include a tab for presenting a dispatch protocol portion of the emergency medical dispatch protocol (e.g., a "KQ" tab or Key Questions tab), a tab for presenting post dispatch instructions and/or critical EMD information (e.g., a "PDI/CEI" tab to provide significant supplemental information such as animal control contact information, law enforcement contact information, and the like), a tab for dispatching life support (e.g., a "DLS" tab), and a tab summarizing the call and/or processing of the call (e.g., "Summary" tab). Some of these other tabs are discussed below with reference to FIGS. 6A-6F and 7. An input 312 may be provided for the dispatcher to indicate when the portion of the emergency medical dispatch protocol presented by the tab 310 has been completed. The input 312 may be a navigation button, as illustrated in FIG. 3, to enable a dispatcher to provide input that indicates to the user interface 300 that the dispatcher is ready to proceed to a next phase of the emergency medical dispatch protocol.

The emergency medical dispatch system user interface 300 may also provide one or more diagnostic tool launch inputs 306. As illustrated, one or more buttons may be provided on the user interface as diagnostic tool launch inputs 306. As will be appreciated by a person of ordinary skill, the diagnostic tool launch inputs 306 may comprise a component other than a button, including familiar user interface components such as a drop down menu, a drop down selection box, a list, a check box, and a radio button. The diagnostic tool launch inputs 306 enable the dispatcher to launch a particular diagnostic tool. Although the emergency medical dispatch protocol may automatically initiate a diagnostic tool based on dispatcher-entered input indicative of one or more responses of the caller, the diagnostic tool launch inputs 306 provide a way for the dispatcher to manually (i.e., anytime, at the dispatcher's discretion) initiate a diagnostic tool. In FIG. 3, a pandemic diagnostic tool launch input 308 is provided. The pandemic diagnostic tool launch input 308 comprises a button on the emergency medical dispatch system user interface 300. The button may include, for example, an icon or a symbol for pandemic virus to indicate that the button is the pandemic diagnostic tool launch input 308, which manually initiates a pandemic diagnostic tool.

Figure 4:
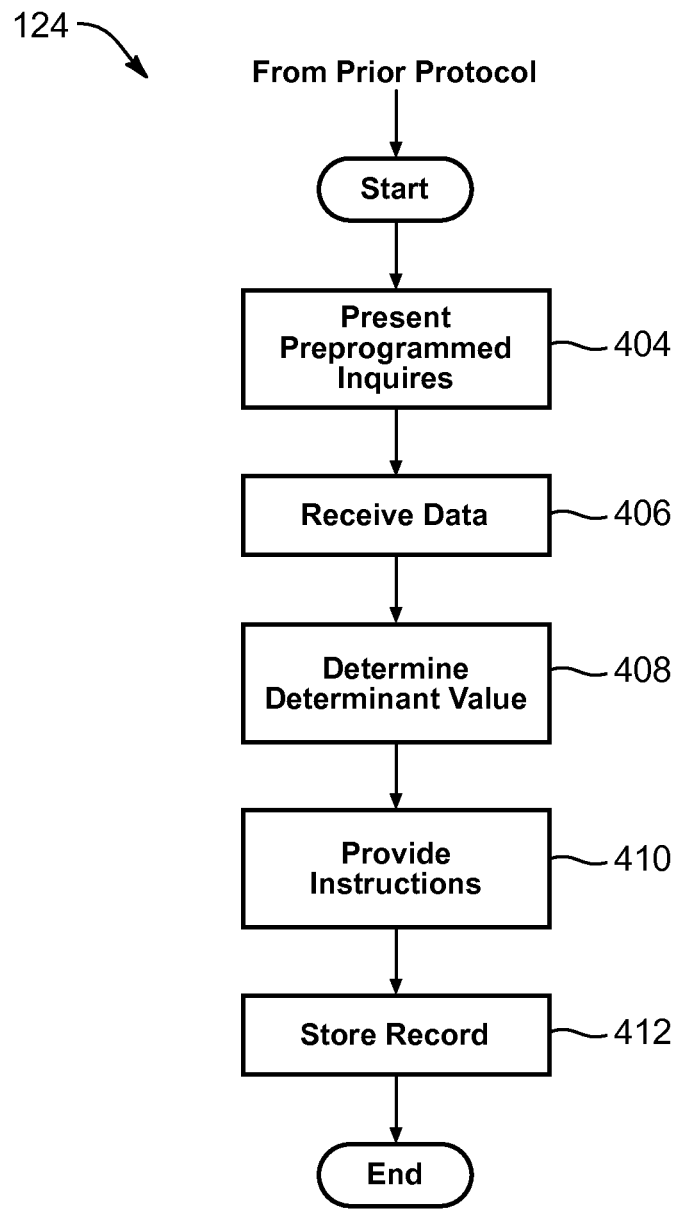
FIG. 4 is a flow diagram of the high-level steps of a dispatch protocol for an emergency dispatch system, according to one embodiment.

FIG. 4 is a flow diagram of the high-level steps of a dispatch protocol 124 for an emergency dispatch system, according to one embodiment. The dispatch protocol 124 may be a pandemic protocol. The dispatch protocol facilitates uniform and consistent gathering of information relating to the patient's chief complaint. Generally, but not always, the dispatch protocol 124 initializes from a prior protocol. The prior protocol may be a case entry protocol. In some instances the prior protocol may be a different dispatch protocol, from which a determination was made to shunt to a more appropriate dispatch protocol. The determination to shunt may be made automatically by the prior protocol or manually by the dispatcher. For a call involving a pandemic illness, the appropriate dispatch protocol 124 may be a pandemic protocol, such as the pandemic protocol described below with reference to FIGS. 5A-5B, and 6A-6F.

In another embodiment, an input component or mechanism may be provided to allow specifying that processing of all emergency calls should include the pandemic protocol. For example, an authorizing authority (e.g., the local health department) may declare, for example, a pandemic outbreak or similar situation requiring more focused attention (e.g., a state of emergency, and instruct that all emergency dispatch calls interrogate regarding the pandemic illness. The input, when provided, may cause the emergency medical dispatch system to automatically shunt processing of all calls to the pandemic protocol, for example initially or after obtaining initial information.

The dispatch protocol 124 may present 404 preprogrammed inquiries according to a pre-scripted interrogation. The preprogrammed inquiries may also be referred to as "Key Questions," targeted to ascertain the severity of the patient's situation or condition and typically based on the chief complaint. Data is received 406 from the dispatcher, as relayed from the caller, following the preprogrammed inquiries asked to the caller by the dispatcher. The data received 406 may correspond to caller responses to the preprogrammed inquiries. The data may be used to determine subsequent questions, or to determine instructions to provide to the dispatcher. The received data is also used by the protocol to determine 408 a determinant value. Intermediate determinant values may be produced as information is received and processed, and the final determinant value may be determined after all information is received and processed.

The dispatch protocol 124 may provide 410 appropriate instructions to be relayed to the caller by the dispatcher. The instructions may comprise post-dispatch instructions for the caller to help prepare the patient for and to expedite the emergency responders' work at the scene. The dispatch protocol may access a database to produce appropriate instructions. Records of the calls are stored 412 for historical reports, for review and analysis of dispatcher performance, and for continued quality assurance control. A record of a call may include, but is not limited to inquiries, responses, and determinant values.

In one embodiment, the dispatch protocol 124 is a pandemic protocol 126. As can be appreciated, the pandemic protocol 126 may be accessed a variety of ways. For example, an emergency medical dispatch protocol may shunt to the pandemic protocol 126 upon receiving indication that pandemic-related symptoms have been reported. In another embodiment, an official authority may control issuance of a pandemic level and/or a pandemic triage level, which may unlock, or otherwise make accessible, the pandemic protocol 126. In one embodiment, the official authority and/or the pandemic level (or flue triage level) may determine whether the pandemic protocol 126 is automatically initiated as a default protocol.

Figure 5A:
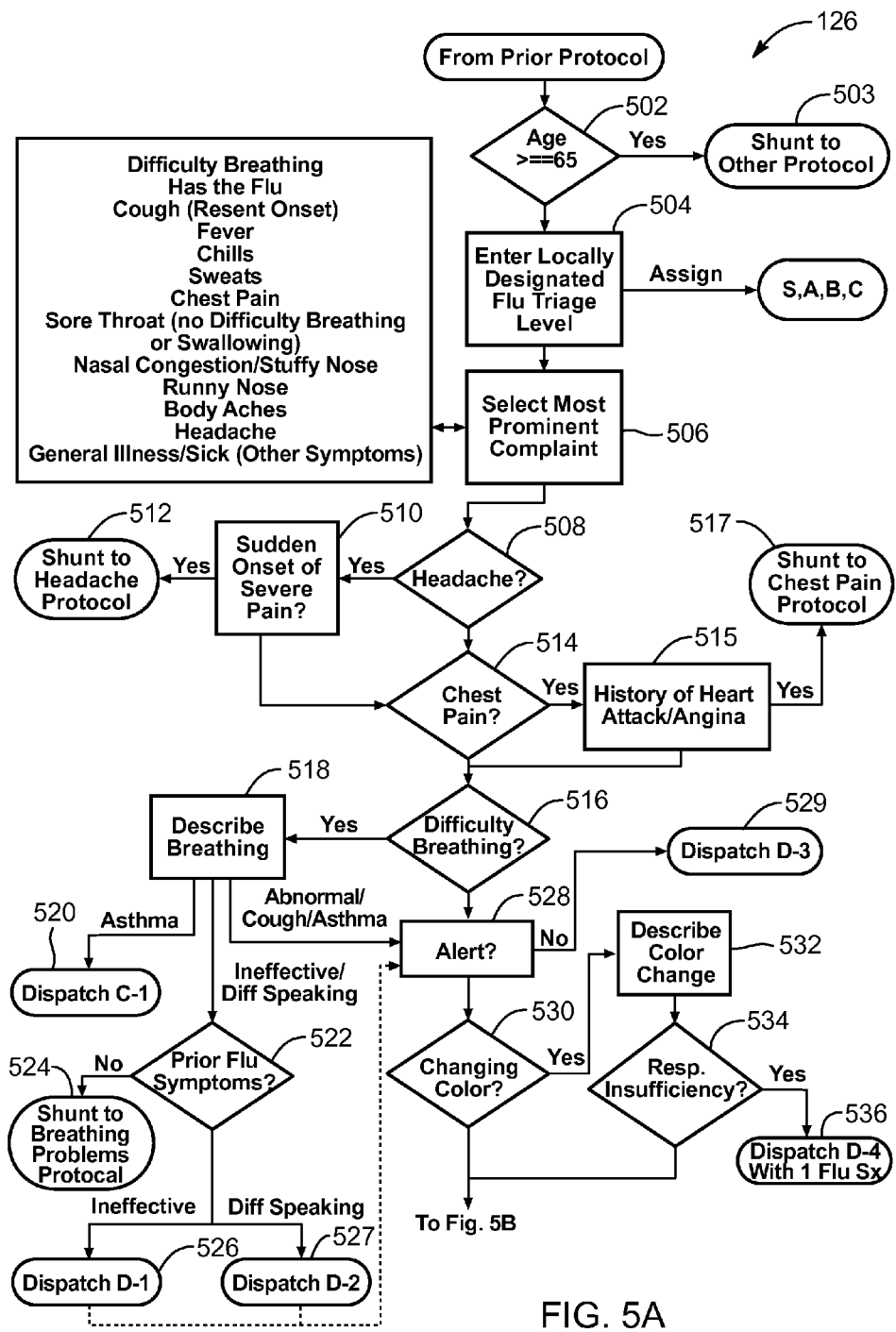
FIGS. 5A-5C are a flow diagram of a pandemic protocol for an emergency dispatch system, according to one embodiment.
Figure 5B:
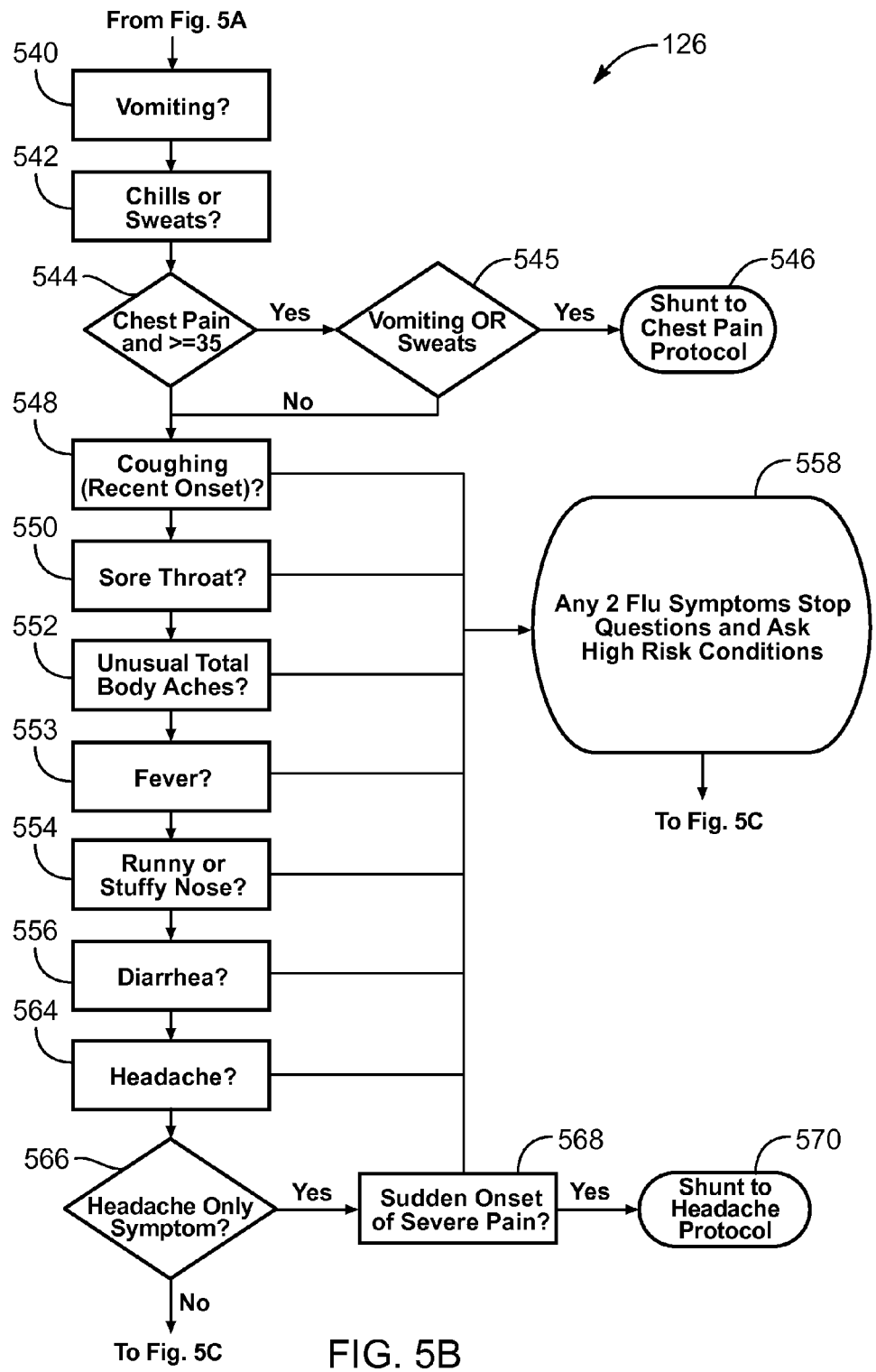
Figure 5C:
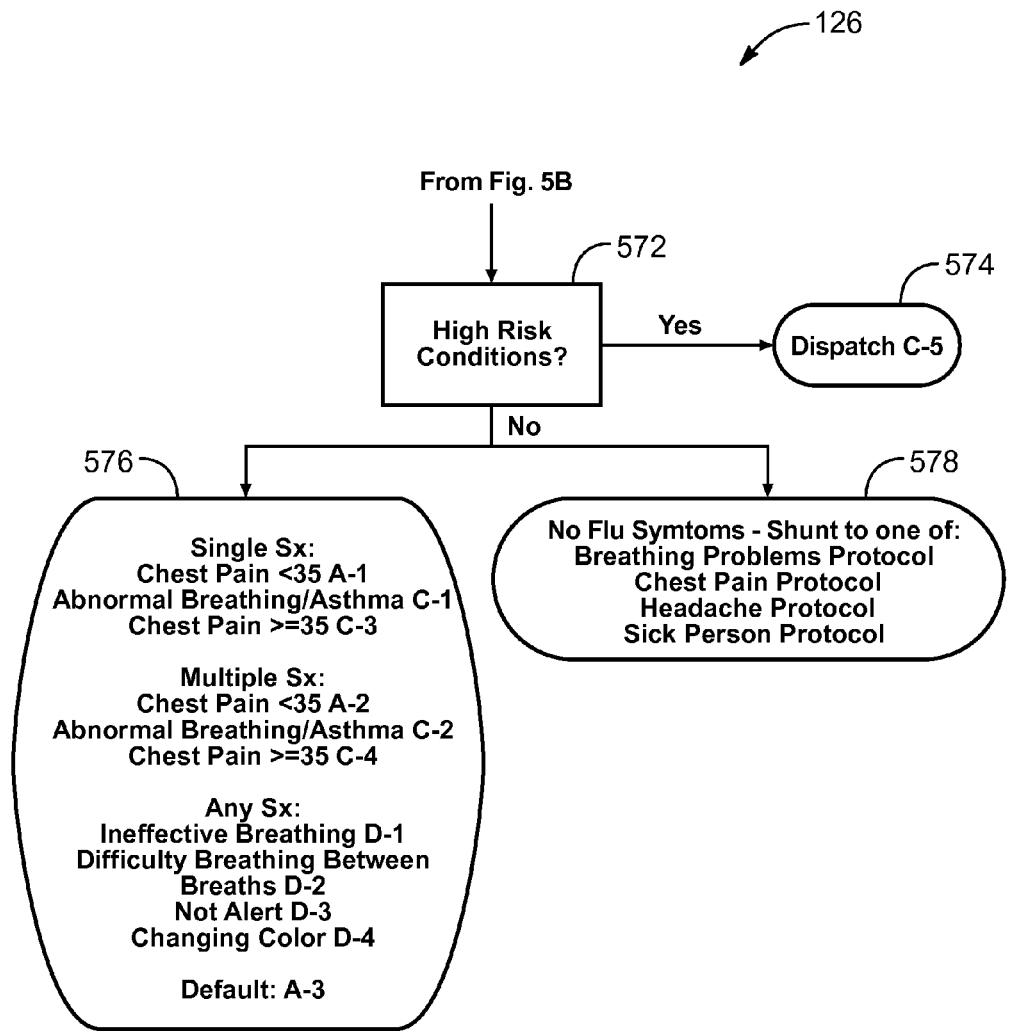

FIGS. 5A-5C are a detailed flow diagram of a method 500 implemented by a pandemic protocol 126 for an emergency dispatch system, according to one embodiment. The pandemic protocol 126 is initialized, typically, from a prior protocol. For example, the pandemic protocol 126 may initialize once the emergency dispatch protocol has traversed all or a portion of a case entry protocol and shunts to the pandemic protocol 126 as the appropriate dispatch protocol for handling the chief complaint of the call. Other dispatch protocols may also shunt to the pandemic protocol 126. In another embodiment, an external factor, such as official authority authorization, may determine whether the pandemic protocol 126 is accessible.

The illustrated embodiment of a pandemic protocol 126 may be configured to facilitate processing of a pandemic involving a severe respiratory infection, such as Influenza (i.e., the "flu"). Accordingly, the discussion of the pandemic protocol 126 in the following paragraphs may be described with particular reference to symptoms relating to Influenza. As can be appreciated, other embodiments may be configured to handle other forms of pandemic outbreaks involving other illnesses (e.g., Anthrax, Ebola, Hepatitis, Yellow Fever, Plague, Smallpox, Rift Valley Fever).

The pandemic protocol 126 of FIGS. 5A, 5B, and 5C may determine 502 whether the patient's age is 65 or older. The patient's age may have been collected during a prior protocol, such as a case entry protocol. In another embodiment, the age information may be collected in the pandemic protocol 126 as needed, such as through a question and response fields on a user interface. If the patient is 65 or older, the pandemic protocol 126 may shunt 503 to another protocol that may be better suited for assisting a dispatcher in handling situations involving older patients. In this manner, the determination 502 of the age-appropriateness of the patient for the pandemic protocol 126 may function as a gatekeeper. These other protocols may be directed to more serious concerns that may need to be addressed in older patients more urgently than a pandemic illness. For example, the other protocols to which the pandemic protocol may shunt 503 may include, but are not limited to, a breathing problems protocol, a chest pain protocol, a headache protocol, and a sick person protocol (e.g., with a specific diagnosis).

If the patient is less than 65 years old, the pandemic protocol 126 may instruct the dispatcher to enter 504 the locally designated pandemic triage level. The locally designated pandemic triage level may indicate the severity of the pandemic. According to one embodiment, there may be four pandemic levels (or pandemic triage levels), which specify internally whether there is a pandemic or not. For example, the four pandemic levels may be designated S, A, B, or C. The dispatcher may enter 504 an input corresponding to the locally designated pandemic triage level that is designated by local health officials and/or other governing or administrative organization.

The dispatcher may also be instructed to select 506 the most prominent complaint of the patient from a list. This instruction may focus the dispatcher, and in turn the caller, to identify what the patient is complaining about most. Of the multiple signs and symptoms that a caller may have, generally one is the most prominent (e.g., cough, body aches, headache, etc.). Information about the patient's most prominent complaint may be obtained through the dispatcher's conversation with the caller. Questions and/or instructions may be provided to guide the dispatcher in the conversation. Exploration of the patient's most prominent complaint may uncover possible symptoms that may be masking the flu and/or that may indicate an underlying issue (e.g., chest pain may indicate a heart attack, a sudden headache may indicate a stroke, etc.).

The pandemic protocol 126 may present to the dispatcher a series of preprogrammed inquiries. The preprogrammed inquiries may be considered a part of a pre-scripted interrogation that is based on a logic tree of the pandemic protocol 126. (The flow diagram of FIGS. 5A-5C may be considered to portray a logic tree, according to one embodiment). The preprogrammed inquiries that are presented as part of a pre-scripted interrogation may depend on dispatcher-entered input as will be described. A pre-scripted interrogation may be considered to be a set of preprogrammed inquiries presented according to traversal of a path along the logic tree.

During a pre-scripted interrogation, the pandemic protocol 126 may receive input from the dispatcher corresponding to caller responses to the preprogrammed inquiries, as was explained above with reference to FIG. 4. The input may be received substantially in real-time, as the dispatcher provides the input. Alternatively or in addition, the input may be received from the emergency medical dispatch system because information sought by the protocol (to determine the path to traverse along the logic tree) may have previously been obtained from the dispatcher via a different protocol. Alternatively, or in addition, the input may be received from a pandemic diagnostic tool. While explicit steps of receiving information are not depicted in FIGS. 5A-5C, an ordinarily skilled artisan will recognize that input may be received at various points in the pandemic protocol 126.

The dispatcher-entered input relates to the emergency call and/or the patient's condition and/or situation. The dispatcher-entered input may affect the path along which the logic tree is traversed. For example, if the dispatcher identifies the patient's most prominent complaint as a headache, the pandemic protocol 126 may make such determination 508 from the input and then the dispatcher may be provided a preprogrammed inquiry 510 to direct to the caller, inquiring of the caller whether the patient's headache occurred as a sudden onset of severe pain. Various paths through one embodiment of a logic tree of a pandemic protocol 126, according to one embodiment, will now be described, including the corresponding preprogrammed inquiries and potential dispatcher-entered input that may be considered.

The pandemic protocol 126 may determine 508 from dispatcher-entered input if the patient's most prominent complaint is a headache. If the determination 508 is that the most prominent complaint is a headache, a preprogrammed inquiry 510, such as "Is the patient's headache a result of a sudden onset of severe pain?", may be provided to gather information whether the patient's headache is a result of a sudden onset of severe pain. If dispatcher-entered input indicates that the caller response is affirmative, the pandemic protocol 126 may shunt 512 to a dispatch protocol that is appropriate for processing headache-related emergency calls. If dispatcher-entered input indicates the caller response is negative, the pandemic protocol 126 may proceed to determine 514 from dispatcher-entered input if the patient's most prominent complaint is chest pain. Similarly, if the determination 508 is that the most prominent complaint is not a headache, the protocol 126 may also proceed to the determination 514 whether the patient's most prominent complaint is chest pain.

If dispatcher-entered input indicates that the patient's most prominent complaint is chest pain, a preprogrammed inquiry 515, such as "Does the patient have a history of heart attack and/or angina?", may be provided to gather information whether the patient has a history of heart disease, cardiac arrest, and/or angina. If dispatcher-entered input indicates that the caller response is affirmative, the pandemic protocol may shunt 517 to a chest pain protocol. If the dispatcher-entered input indicates that the caller response is negative, or if the determination 514 is that the patient's chief complaint is not chest pain, the pandemic protocol 126 may proceed by determining 516 if the patient's most prominent complaint is difficulty breathing.

The pandemic protocol 126 may determine 516 from dispatcher-entered input if the patient's most prominent complaint is difficulty breathing. If the most prominent complaint is difficulty breathing, a preprogrammed inquiry 518, such as "Describe the patient's breathing," may be presented to gather additional information about the patient's breathing. At least three different paths may be possible from the preprogrammed inquiry 518, depending on the caller's response and the input provided by the dispatcher. First, if dispatcher-entered input indicates the caller response describes the patient's breathing as asthmatic or that the patient's difficulty breathing relates to asthma, a determinant value C-1 may be determined 520 by the pandemic protocol 126 as an appropriate determinant value for an emergency dispatch response for the call.

Second, if dispatcher-entered input indicates the caller response describes the patient's breathing as ineffective and/or difficulty speaking, a preprogrammed inquiry 522, such as "Did s/he have any flu symptoms prior to this?" may be presented to gather information as to whether any other flu symptoms were previously reported. If the dispatcher-entered input indicates the caller response was that there were not flu symptoms previously reported, the pandemic protocol 126 may shunt 524 to a dispatch protocol that may be appropriate for processing emergency calls involving breathing problems. If the dispatcher-entered input indicates the caller response was that there are prior flu symptoms, a determinant value D-1 may be determined 526 by the pandemic protocol 126 as an appropriate determinant value for an emergency dispatch response for the call in the case of a situation described by the caller as ineffective breathing or a determinant value D-2 may be determined 527 by the pandemic protocol 126 as an appropriate determinant value for an emergency dispatch response for the call in the case of a situation described by the caller as difficulty speaking. In some embodiments, the protocol 126 may end after the determinant values D-1 or D-2 is determined 526, 527. In other embodiments, the protocol 126 may continue by presenting an additional preprogrammed inquiry 528, such as "Is the patient Alert?" After determining 526, 527 one of the determinant values D-1 or D-2 and presenting the additional preprogrammed inquiry 528, the protocol 126 may end, regardless of any response (or input indicative of a response) to the preprogrammed inquiry 528. In other embodiments, the protocol 126 may continue after presenting the preprogrammed inquiry 528, as will be described below.

Third, if dispatcher-entered input indicates the caller response describes the patient's breathing as abnormal and/or accompanied by a cough, the pandemic protocol 126 may proceed to present a preprogrammed inquiry 528, such as "Is the patient Alert?" If the dispatcher-entered input indicates the patient is not alert, a determinant value D-3 may be determined 529 by the pandemic protocol 126 as an appropriate determinant value for an emergency dispatch response for the call.

If the dispatcher-entered input indicates that the patient is alert, the pandemic protocol 126 may determine 530 if the chief complaint is that the patient is changing color. If the dispatcher-entered input indicates the patient is changing color, the pandemic protocol 126 may present a preprogrammed inquiry 532, such as "Describe the color change," to seek information concerning the color change the patient is experiencing. The pandemic protocol 126 may then determine 534 respiratory insufficiency based on input corresponding to the description of the color change. Respiratory insufficiency (or lack of oxygen perfusion to the blood) may occur when the breathing that is taking place is insufficient, regardless of whether a difficulty in breathing (see determination 516) is reported. Shallow breathing or agonal breathing are examples where respiratory insufficiency may occur. The signs (e.g., color change) may indicate insufficient oxygen getting to the blood, regardless of the cause. The cause may be less important than the effect. If the determination 534 is that respiratory insufficiency is present, the pandemic protocol 126 may determine that an appropriate determinant value for an emergency dispatch response to the call is D-4 and the determinant value D-4 may be presented or otherwise provided. Indication of a single flu symptom may accompany determinant value and/or the dispatch response.

If the determination 530 is that the patient is not changing color the pandemic protocol may present a preprogrammed inquiry 540 such as "Is the patient vomiting?" and a preprogrammed inquiry 542 such as "Does the patient have chills or sweats?". Dispatcher-entered input may be received for both of these preprogrammed inquiries 540, 542. The pandemic protocol 126 may determine 544 from dispatcher-entered input if the patient's most prominent complaint is chest pain. If the determination 536 is that the patient's most prominent complaint is chest pain and the patient is thirty-five years old or older, the pandemic protocol 126 may determine 545 from dispatcher-entered input whether the patient is vomiting and/or experiencing chills or sweats. If the determination 545 is that the patient is vomiting and/or experiencing chills or sweats, the pandemic protocol may shunt to a dispatch protocol that is appropriate for processing emergency calls involving chest pain.

If dispatcher-entered input indicates the patient is not vomiting and not experiencing chills or sweats, the pandemic protocol 126 may proceed to a series of preprogrammed inquires 548, 550, 552, 553, 554, 556, 564 that inquire about particular symptoms the patient may be manifesting that indicate the patient may have Influenza. The preprogrammed inquiries may include, but are not limited to the inquiry 548 "Has the patient experienced a recent onset of coughing?", the inquiry 550 "Does the patient have a sore throat?", the inquiry 552 "Does the patient have unusual total body aches?", the inquiry 553 "Does the patient have a fever?", the inquiry 554 "Does the patient have a runny or stuffy nose?", the inquiry 556 "Does the patient have diarrhea?", and the inquiry 564 "Does the patient have a headache?" In the illustrated embodiment, the preprogrammed inquiries 548, 550, 552, 553, 554, 556, 564 may relate to the list of the potential most prominent complaints of the patient that may be selected 506 by the dispatcher. Accordingly, not only is the most prominent (e.g., the most severe, bothersome, alarming, etc.) symptom the patient may be experiencing identified, the pandemic protocol 126 may also facilitate identifying other of the patient's symptoms, which may be in addition to the chief complaint. As noted previously, in another embodiment the pandemic protocol 126 may be configured to facilitate processing of emergency calls related to a pandemic illness other than Influenza, in which case the preprogrammed inquiries may be directed to symptoms of the other pandemic illness.

If the caller responses to the preprogrammed inquiries, and corresponding dispatcher-entered input, indicate that the patient has any two flu symptoms, then the pandemic protocol 126 may stop 558 questions and proceed to instruct the dispatcher to inquire about high risk conditions 572. The emergency medical dispatch system may have already determined that the patient likely has the flu, and therefore a lower response to the situation is contemplated. The high risk conditions 572 may be conditions that make the flu more high risk than for typical patients to queue up a higher dispatch response if needed. Examples of high risk conditions may include, but are not limited to: the patient is 12 yrs old or younger; diabetes; sickle cell disease (sickle cell anemia); neurological disease (affecting swallowing or breathing); pregnancy; and immune system disorders. Questions pertaining to high risk conditions allow for a higher response in the situations where it is most warranted.

After the preprogrammed inquiries 548, 550, 552, 553, 554, 556, 564, the pandemic protocol 126 may determine 566 whether the only flu symptom that the patient is manifesting is a headache. If so, a preprogrammed inquiry 568, such as "Is the patient's headache a result of a sudden onset of severe pain?", may be provided to gather information whether the patient's headache is a result from a sudden onset of severe pain. If dispatcher-entered input indicates that the caller response is affirmative, the pandemic protocol 126 may shunt 570 to a dispatch protocol that is appropriate for processing headache-related emergency calls. The headache protocol may, for example, catch an occasional situation of a stroke that may be masked by flu symptoms. If dispatcher-entered input indicates the caller response is negative, the pandemic protocol 126 may proceed to instruct the dispatcher to ask about high risk conditions 572.

If dispatcher-entered input indicates that the patient has high risk conditions, then a determinant value C-5 may be determined 574 by the pandemic protocol 126 as an appropriate determinant value for an emergency dispatch response for the call.

If the dispatcher-entered input indicates that the patient is not manifesting any high risk conditions, but is manifesting one of several symptomatic scenarios, an appropriate determinant value may be determined 576. For example, if the patient is manifesting a single flu symptom and one of either chest pain or abnormal breathing, an appropriate determinant value may be determined. In particular, if the patient is manifesting a single flu symptom and also is manifesting chest pain, and the patient is under 35 years of age, a determinant value A-1 may be determined 576, or if the patient is over 35 years of age, a determinant value C-3 may be determined 576. If the patient is manifesting a single flu symptom and is also manifesting abnormal breathing/asthma, a determinant value C-1 is determined 576.

The patient may also be manifesting multiple flu symptoms, in which case the determinant value that may be determined may be different than for single flu symptoms. For example, if the patient is manifesting multiple flu symptoms and also is manifesting chest pain, and the patient is under 35 years of age, a determinant value A-2 may be determined 576, or if the patient is over 35 years of age, a determinant value C-4 may be determined 576. If the patient is manifesting multiple flu symptoms and is also manifesting abnormal breathing/asthma, a determinant value C-2 is determined 576.

If the foregoing formulas for determination 576 of an appropriate determinant value are not relevant, then other formulas for the determination 576 are possible. For a patient manifesting any flu symptoms and manifesting ineffective breathing, a determinant value D-1 is determined. For a patient manifesting any flu symptoms and manifesting difficulty breathing, a determinant value D-2 is determined. For a patient manifesting any flu symptoms and who is not alert, a determinant value D-3 is determined. For a patient manifesting any flu symptoms and who is changing color, a determinant value D-4 may be determined. In some embodiments, a default determinant value, such as A-3, may be determined for instances where the formulas for the determination 576 are not applicable.

In the event that the dispatcher-entered input indicates the patient is not manifesting any flu symptoms (including not manifesting a headache), the pandemic protocol 126 may shunt 578 to a different dispatch protocol. For example, the pandemic protocol 126 may shunt 578 to a dispatch protocol specific to one of breathing problems, chest pain, headache, or sick person. A subset of various protocols may be presented for selection by the dispatcher. The subset of protocols may be determined based on the initial apparent presentation of a flu condition.

FIGS. 6A-6F are a user interface 300 of an emergency medical dispatch system at various points as the emergency medical dispatch system presents a pre-scripted interrogation, traversing one path of a logic tree of a pandemic protocol, according to one embodiment. As previously explained above, with reference to FIG. 3, the emergency medical dispatch system user interface 300 allows a dispatcher to interface with the emergency medical dispatch protocol. In particular, in the illustrated embodiment, the user interface 300 is facilitating traversal of a pandemic protocol. The user interface 300 presents a tab 310b that is configured to present preprogrammed inquiries (e.g., Key Questions) as part of a pre-scripted interrogation of a dispatch protocol. The particular questions presented may depend on the dispatch protocol, in this case the pandemic protocol, and the path along a logic tree of the dispatch protocol that may be traversed based on caller responses to the preprogrammed inquiries, as explained above with reference to FIGS. 5A-5C. Typically, but not always, the user interface 300 will present tab 310b upon completion of the case entry protocol on tab 310a (i.e., the "Entry" tab"). If sufficient information is available to identify a chief complaint, the emergency medical dispatch protocol may shunt to an appropriate dispatch protocol. In this case, the emergency medical dispatch protocol has shunted to the pandemic protocol, and the user interface presents tab 310b and initializes the pandemic protocol.

Figure 6A:
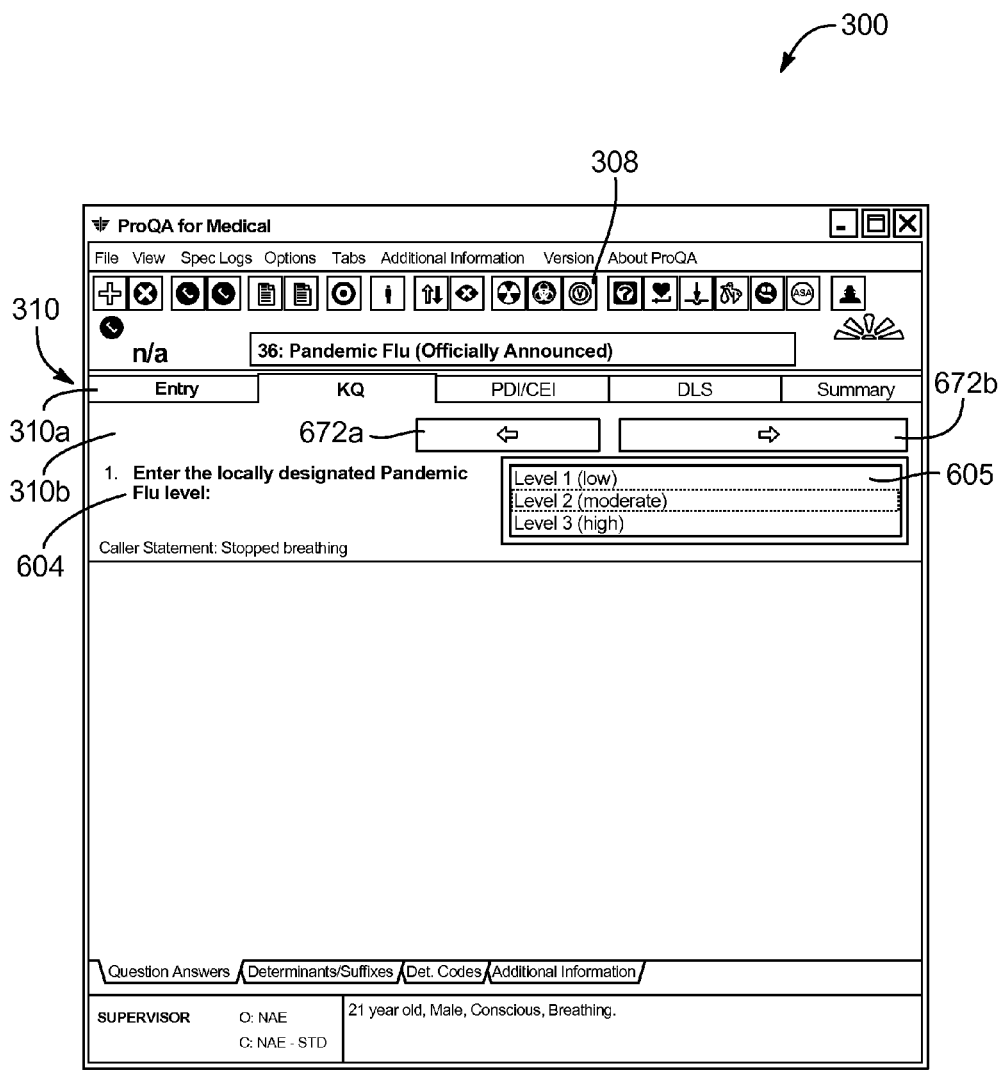
FIGS. 6A-6F are a user interface of an emergency medical dispatch system, at various points, as the emergency medical dispatch system traverses one path of a logic tree of a pandemic protocol for an emergency dispatch system.

FIG. 6A shows the user interface 300 presenting an instruction 604 for the dispatcher to enter the locally designated pandemic triage level (e.g., pandemic flu level). An input field 605 enables the dispatcher to quickly and easily enter the appropriate level. In the illustrated embodiment, the input field 605 presented is a list box providing a list of acceptable inputs. As will be appreciated, the input field 605 may be any of a number of appropriate input field types, including but not limited to text fields, text boxes, menus, drop down menus, drop-down selection boxes, lists, buttons, check boxes, and radio buttons. In FIG. 6A, the Pandemic Flu level "Level 2 (moderate)" is selected.

The user interface 300 may present navigation buttons 672a, 672b to enable the dispatcher to indicate to the user interface to navigate back or forward, respectively, in the emergency dispatch protocol. The dispatcher can select the navigation button 672b to indicate to the user interface 300 that the dispatcher is ready to proceed in the protocol. The dispatcher can select the navigation button 672a to go back in the protocol. Accordingly, when the dispatcher selects the forward navigation button 672b, the protocol advances and the user interface 300 may present a next instruction and/or preprogrammed inquiry.

The user interface 300 may also present diagnostic tool launch inputs, including a pandemic diagnostic tool launch input 308. As described previously, the pandemic diagnostic tool may enable a dispatcher to manually launch a pandemic diagnostic tool at any point during the emergency medical dispatch protocol, including during a dispatch protocol such as a pandemic protocol.

Figure 6B:
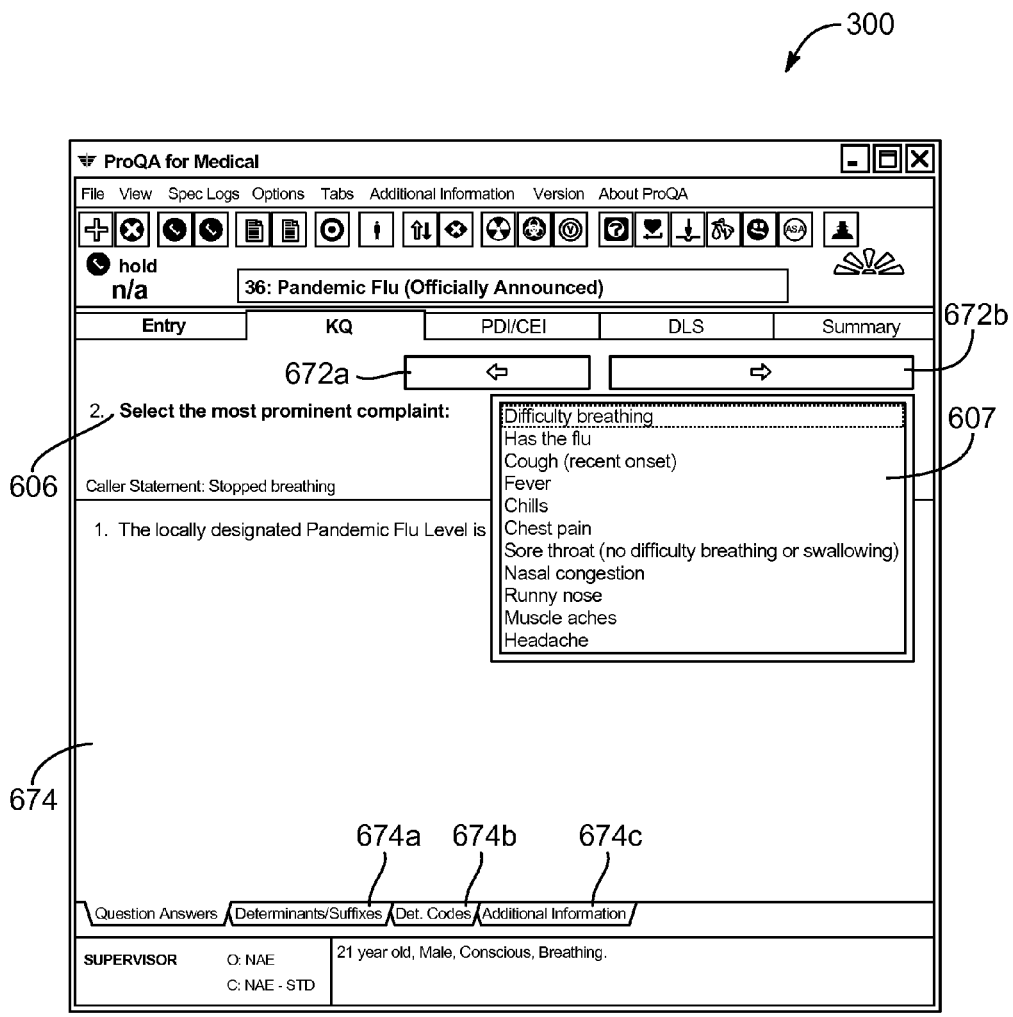

FIG. 6B shows the user interface 300 presenting an instruction 606 for the dispatcher to enter the most prominent complaint. An input field 607 enables the dispatcher to enter the patient's most prominent complaint. In the illustrated embodiment, the input field 607 provided is a list box presenting a list of acceptable most prominent complaints that may be provided as input. As will be appreciated, the input field 607 may be any of a number of appropriate input field types, including but not limited to text fields, text boxes, menus, drop down menus, drop-down selection boxes, lists, buttons, check boxes, and radio buttons. In FIG. 6B, the list of potential most prominent complaints includes "difficulty breathing," "has the flu," "cough (recent onset)," "fever," "chills," "chest pain," "sore throat (no difficulty breathing or swallowing)," "nasal congestion," "runny nose," "muscle aches," and "headache". In FIG. 6B, the most prominent complaint selected is "Difficulty breathing," and this input may be provided to the protocol upon the dispatcher selecting the forward navigation button 672b.

The user interface 300 may also present an answers pane 674 to display input received in relation to previous instructions and/or preprogrammed inquiries. For example, the answers pane 674 of FIG. 6B displays the dispatcher-entered input provided for instruction 604; e.g., "1. The locally designated Pandemic Flu Level is 2 (moderate)." The answers pane 674 enables a dispatcher to quickly review previous responses for accuracy and to thereby improve understanding of the situation and/or patient condition reported by the caller. If the dispatcher were to inadvertently select an incorrect locally designate Pandemic Flu Level, the dispatcher can navigate back in the protocol by selecting the back navigation button 672a and then select a correct Pandemic Flu Level. Other panes may also be available for presentation to a dispatcher, to provide additional information relating to processing a given emergency call, including a "Determinants/Suffixes" pane 674a, a "Determinant Codes" pane 674b, and an "Additional Information" pane 674c.

Figure 6C:
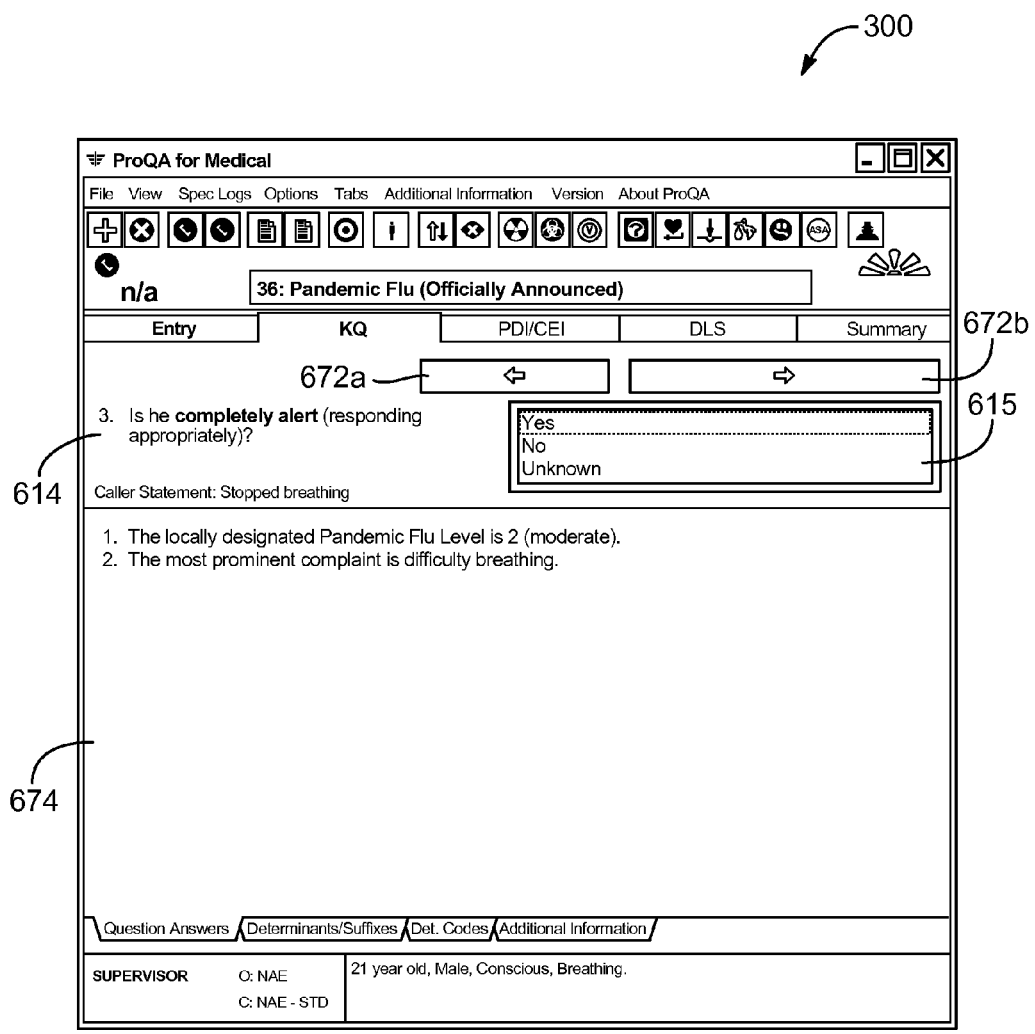

FIG. 6C illustrates the user interface 300 presenting a preprogrammed inquiry 614 "Is he [or she] completely alert (responding appropriately)?" for the dispatcher to relay to the caller. An input field 615 enables the dispatcher to enter input indicative of the caller's response to the preprogrammed inquiry 614. In the illustrated embodiment, the input field 615 provided is a list box presenting a list of acceptable inputs. As will be appreciated, the input field 615 may be any of a number of appropriate input field types, including but not limited to text fields, text boxes, menus, drop down menus, drop-down selection boxes, lists, buttons, check boxes, and radio buttons. In FIG. 6C, the list of acceptable inputs may include "Yes," "No," and "Unknown." As before, the answers pane 674 may display previously entered input, including "2. The most prominent complaint is difficulty breathing." The dispatcher can select the navigation button 672b to indicate to the user interface 300 that the dispatcher is ready to proceed in the protocol. The dispatcher can select the navigation button 672a to go back in the protocol.

Figure 6D:
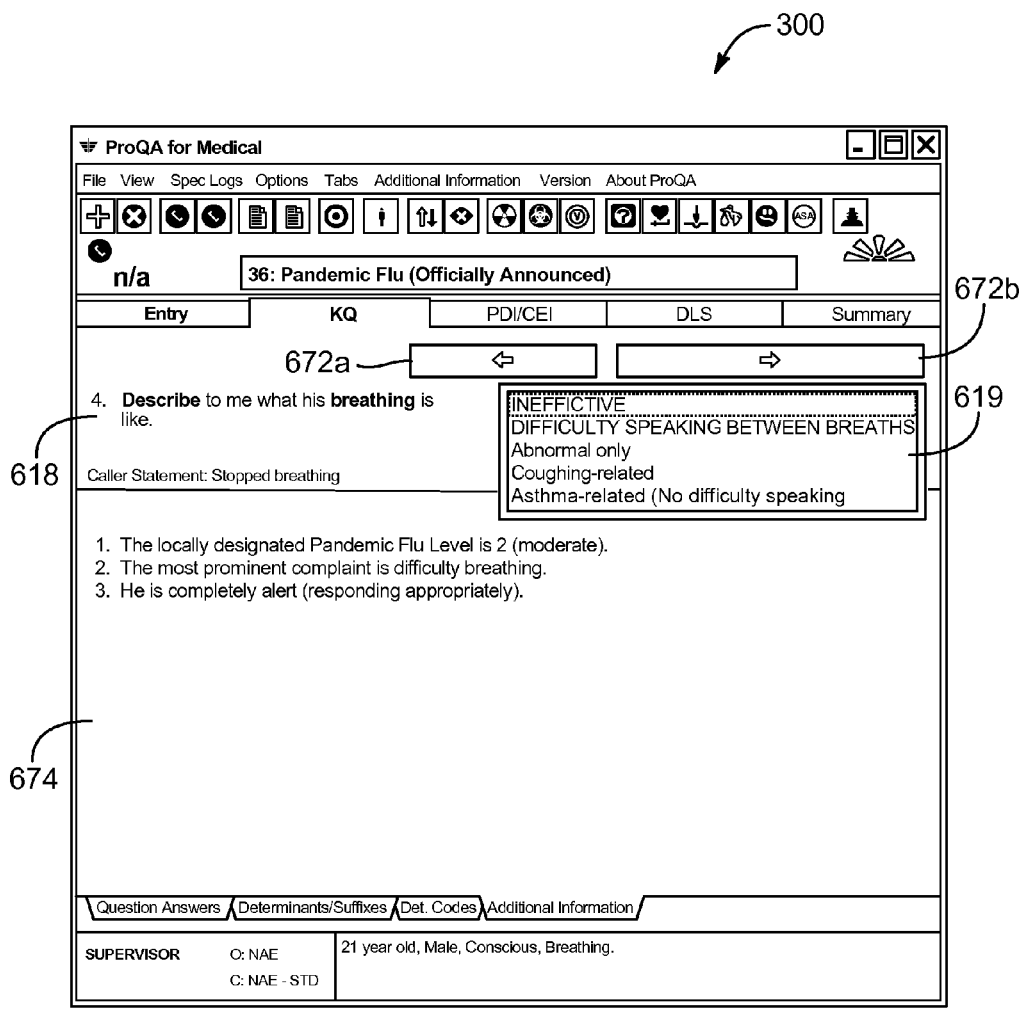

FIG. 6D illustrates the user interface 300 presenting a preprogrammed inquiry 618 "Describe to me what his [or her] breathing is like" for the dispatcher to relay to the caller. The pandemic protocol determined 516 (see FIG. 5A) that the patient's most prominent complaint is "difficulty breathing," and accordingly proceeded to present a preprogrammed inquiry 618 aimed to further explore that most prominent complaint and gather additional information. An input field 619 enables the dispatcher to enter input indicative of the caller's response to the preprogrammed inquiry 618. In the illustrated embodiment, the input field 619 provided is a list box presenting a list of acceptable inputs. As will be appreciated, the input field 619 may be any of a number of appropriate input field types, including but not limited to text fields, text boxes, menus, drop down menus, drop-down selection boxes, lists, buttons, check boxes, and radio buttons. In FIG. 6D, the list of acceptable inputs may include "Coughing-related", "Abnormal only," "Difficulty speaking between breaths," "Ineffective," and "Asthma related."

As before, the answers pane 674 may display previously entered input, including "3. He [or she] is completely alert (responding appropriately)." The dispatcher can select the navigation button 672b to indicate to the user interface 300 that the dispatcher is ready to proceed in the protocol. The dispatcher can select the navigation button 672a to go back in the protocol.

Figure 6E:
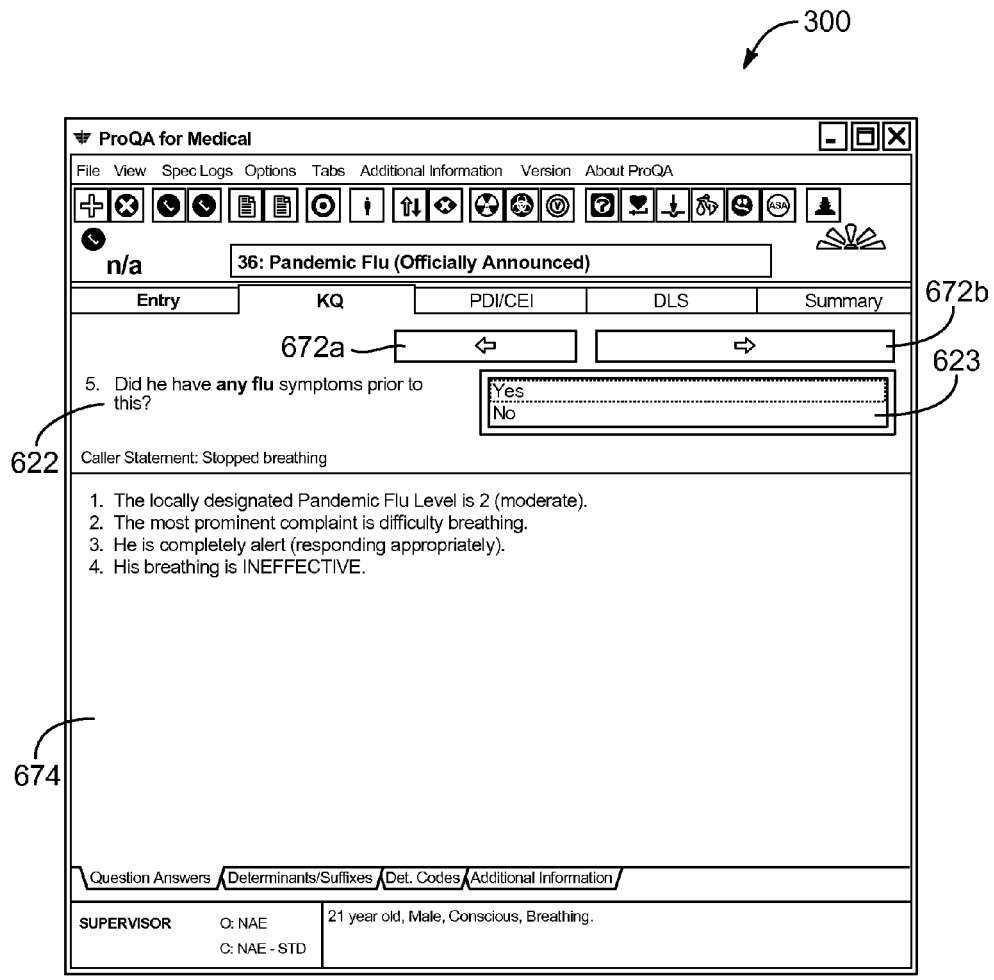

FIG. 6E illustrates the user interface 300 presenting a preprogrammed inquiry 622 "Did he [or she] have any flu symptoms prior to this?" for the dispatcher to relay to the caller. As illustrated in the answers pane 674, dispatcher-entered input indicates that the caller described the patient's breathing as "INEFFECTIVE." According to FIG. 5A, the next progression of the pandemic protocol when the patient's breathing is described as ineffective in response to preprogrammed inquiry 618 "Describe to me what his breathing is like" may be to obtain information concerning prior flu symptoms. An input field 623 may be provided to enable the dispatcher to enter input indicative of the caller's response to the preprogrammed inquiry 622. In the illustrated embodiment, the input field 623 provided is a list box presenting a list of acceptable inputs. As will be appreciated, the input field 623 may be any of a number of appropriate input field types, including but not limited to text fields, text boxes, menus, drop down menus, drop-down selection boxes, lists, buttons, check boxes, and radio buttons. In FIG. 6E, the list of acceptable inputs may include "Yes" and "No." The dispatcher can select the navigation button 672b to indicate to the user interface 300 that the dispatcher is ready to proceed in the protocol. The dispatcher can select the navigation button 672a to go back in the protocol.

Figure 6F:
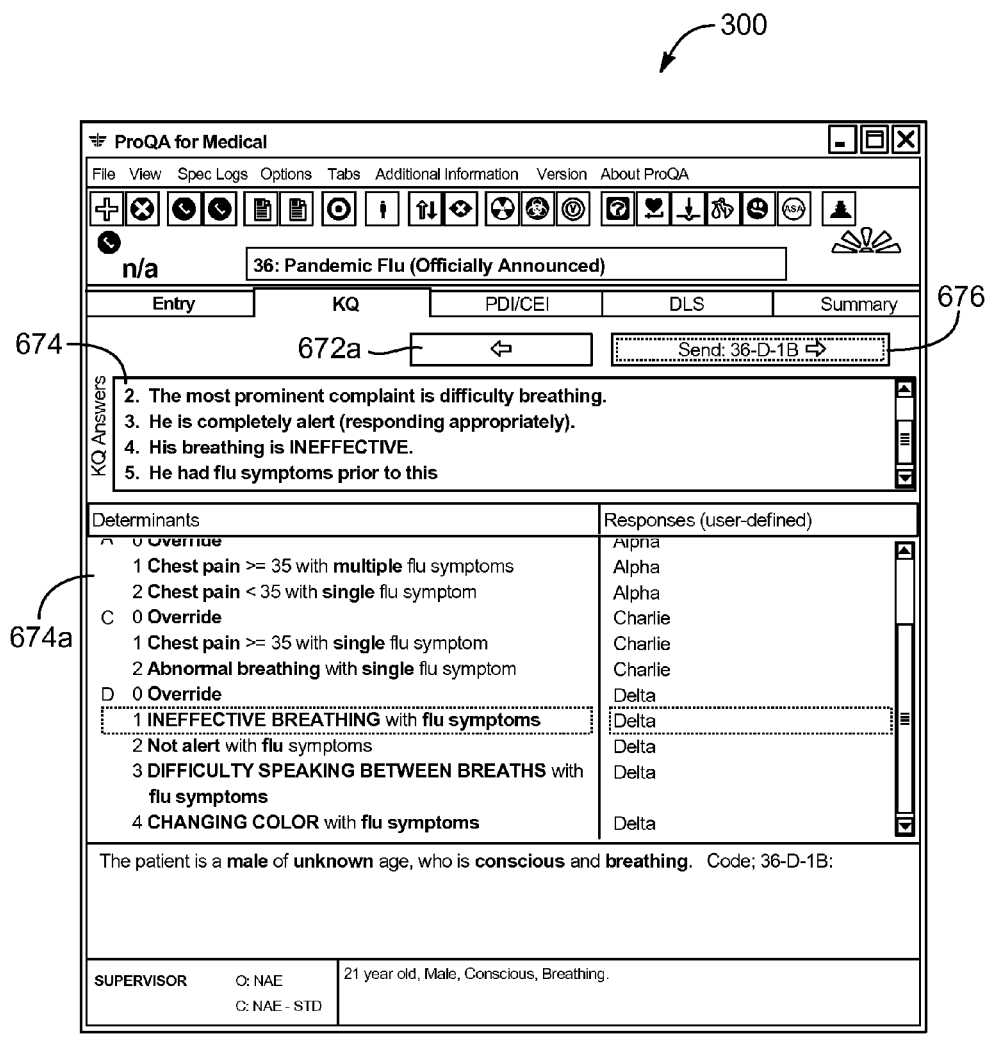

FIG. 6F illustrates the user interface 300 presenting a determinant value that can be used to generate an appropriate emergency dispatch response. As indicated in the answers pane 674, dispatcher-entered input indicated that the patient had experienced flu symptoms prior to the current situation. The pandemic protocol determines that an appropriate determinant value is D-1 when the patient is experiencing ineffective breathing with prior flu symptoms. The user interface 300 may present a determinant code pane 674a when a final determinant value is assigned by the protocol. The determinant code pane 674a may provide a listing of potential determinant codes and/or determinant values for a given situation and may indicate (e.g., highlight) an appropriate determinant code and/or determinant value as determined by the protocol. Moreover, the user interface 300 may also present a "Send" button 676 to send the assigned determinant value to generate an emergency dispatch response. The assigned determinant value may be sent to another portion of the emergency medical dispatch protocol and/or the CAD system for transmission to the emergency responders. The dispatcher can select the navigation button 672a to go back in the protocol.

Figure 7:
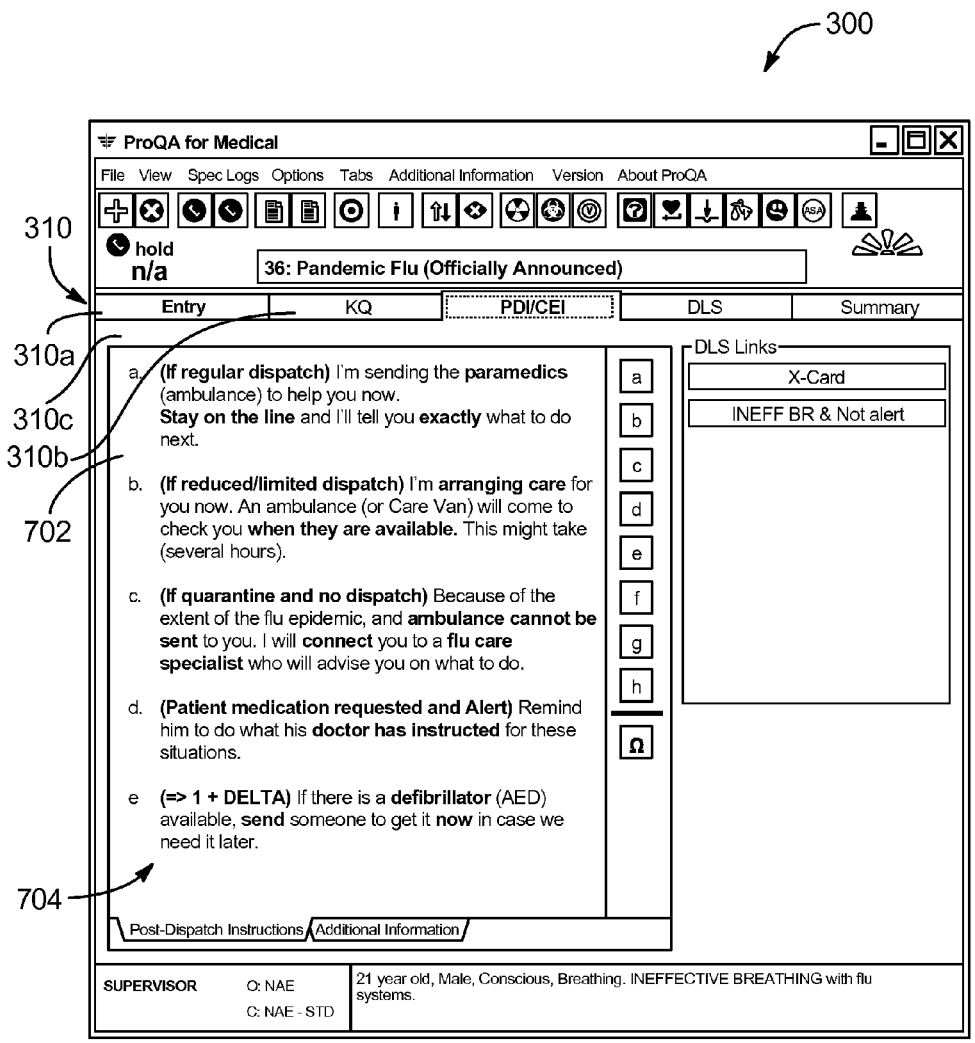
FIG. 7 is a user interface of an emergency medical dispatch system, according to one embodiment, presenting post-dispatch instructions

FIG. 7 is a user interface 300 of an emergency medical dispatch system, according to one embodiment, presenting post-dispatch instructions. The user interface 300 presents a tab 310c that is configured to present post-dispatch instructions 704. Typically, but not exclusively, the user interface 300 will present tab 310c (i.e., "PDI/CEI" tab) upon completion of a dispatch protocol, such as the pandemic protocol, on tab 310b (i.e., the "Key Questions"). The tab 310c may include a post-dispatch instructions pane 702 including one or more post-dispatch instructions 704 for the dispatcher to relay to the caller. The post-dispatch instructions may aid the caller in preparing the patient to receive expedited care upon the arrival of the emergency responders at the scene.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer-implemented method to guide a dispatcher when communicating vocally with a caller via a communication device regarding a medical emergency involving a patient manifesting symptoms of a pandemic illness and for dispatching an emergency response by emergency responders, the computer-implemented method comprising:

presenting on a dispatch center computer device a pre-scripted interrogation comprising a plurality of preprogrammed inquiries for the dispatcher to ask the caller to systematically obtain a description of the medical emergency including information concerning symptoms of the pandemic illness that the patient is manifesting, the description of the medical emergency comprising caller responses to the plurality of preprogrammed inquiries, wherein the dispatch center computer device includes a logic tree configured to determine the preprogrammed inquiries of the pre-scripted interrogation and automatically determine one of a plurality of pre-established determinant values based on dispatcher-entered input representative of caller responses to the preprogrammed inquires;

receiving dispatcher-entered input on the dispatch center computer device representative of caller responses to the preprogrammed inquiries of the pre-scripted interrogation;

assigning on the dispatch center computer device the pre-established determinant value determined by the logic tree and the pre-scripted interrogation; and generating an emergency medical dispatch response by emergency responders based on the assigned pre-established determinant value.

2. The computer-implemented method of claim 1, further comprising presenting preprogrammed inquiries of the pre-scripted interrogation as the method traverses a path along the logical tree of the pre-scripted interrogation based on caller responses to the preprogrammed inquiries, and wherein the path along the logical tree ends at the pre-established determinant value.

3. The computer-implemented method of claim 1, further comprising providing preprogrammed inquiries to the dispatcher via a user interface on an output device of the dispatch center computer device.

4. The computer-implemented method of claim 1, further comprising providing preprogrammed inquiries to said dispatcher on a medium readable by the dispatcher.

5. The computer-implemented method of claim 1, further comprising providing on the dispatch center computer device instructions to the dispatcher, including instructions to inquire for specific information from the caller and to provide input to the dispatch center computer device corresponding to the specific information received from the caller.

6. The computer-implemented method of claim 5, wherein the instructions to the dispatcher provided by the dispatch center computer device include an instruction to enter the locally designated pandemic triage level.

7. The computer-implemented method of claim 5, wherein the instructions to the dispatcher provided on the dispatch center computer device include an instruction to enter the most prominent complaint of the patient.

8. The computer-implemented method of claim 1, wherein the logic tree determining the one of a plurality of pre-established determinant values includes determining from dispatcher-entered input whether the patient's most prominent complaint is one of a headache, difficulty breathing and chest pain, and if so, the pre-scripted interrogation includes presenting preprogrammed inquiries for the dispatcher to ask the caller to systematically obtain additional description relating to the most prominent complaint.

9. The computer-implemented method of claim 8, wherein if the most prominent complaint of the patient is a headache, the preprogrammed inquires of the pre-scripted interrogation include asking the caller to indicate whether the headache occurred as a sudden onset of severe pain.

10. The computer-implemented method of claim 8, wherein if the most prominent complaint of the patient is difficulty breathing, the preprogrammed inquires of the pre-scripted interrogation include:
    asking the caller to identify the quality of the patient's breathing; and
    asking the caller whether the patient has had any prior flu symptoms.

11. The computer-implemented method of claim 8, wherein if the most prominent complaint of the patient is chest pain and the patient is thirty-five years old or older, the preprogrammed inquires of the pre-scripted interrogation include:
    asking the caller whether the patient is vomiting; and
    asking the caller whether the patient has chills or sweats.

12. The computer-implemented method of claim 1, wherein the preprogrammed inquires of the pre-scripted interrogation include:
    asking the caller whether the patient is completely awake; and
    asking the caller whether the patient is changing color.

13. The computer-implemented method of claim 1, wherein the preprogrammed inquires of the pre-scripted interrogation include inquiries asking the caller to identify whether the patient has flu symptoms including: vomiting, sweats or chills, fever, recent onset of coughing, sore throat, body aches, runny or stuffy nose, diarrhea, and headache.

14. The computer-implemented method of claim 1, further comprising providing post-dispatch instructions to the caller.

15. A computer system to guide a dispatcher when communicating with a caller vocally via a communication device regarding a medical emergency involving a patient manifesting symptoms of a pandemic illness and for dispatching an emergency response by emergency responders, the computer system comprising:
    a processor;
    an output device in communication with the processor;
    an input device in communication with the processor;
    a memory in communication with the processor, the memory comprising:
        a pandemic protocol module comprising a logic tree that is configured to determine one of a plurality of pre-established determinant values, the pandemic protocol module configured to:
            present on the output device a pre-scripted interrogation comprising a plurality of preprogrammed inquiries for the dispatcher to ask the caller to systematically obtain a description of the medical emergency including information concerning symptoms of the pandemic illness that the patient is manifesting, wherein the description of the medical emergency comprises caller responses to the plurality of preprogrammed inquiries, wherein the preprogrammed inquiries of the pre-scripted interrogation are determined according to the logic tree, and wherein one of the plurality of pre-established determinant values is determined in accordance with the logic tree based on dispatcher-entered input representative of caller responses to the preprogrammed inquires,
            receive via the input device dispatcher-entered input representative of caller responses to the preprogrammed inquiries of the pre-scripted interrogation, and
            assign the pre-established determinant value determined by the logic tree and the pre-scripted interrogation.

16. The computer system of claim 15, wherein said preprogrammed inquiries of the pre-scripted interrogation are provided as a path along the logic tree is traversed based on responses to the preprogrammed inquiries, and wherein the path along the logical tree ends at the pre-established determinant value.

17. The computer system of claim 15, the memory further comprising a user interface to be presented on the output device and configured to facilitate presentation of preprogrammed inquiries and to facilitate receiving dispatcher-entered input.

18. The computer system of claim 15, wherein the pandemic protocol module is further configured to provide on the output device instructions to the dispatcher, including instructions to inquire for specific information from the caller, and to provide input to the computer system corresponding to the specific information received from the caller.

19. The computer system of claim 18, wherein the instructions to the dispatcher include an instruction to enter the locally designated pandemic triage level.

20. The computer system of claim 18, wherein the instructions to the dispatcher include an instruction to enter the most prominent complaint of the patient.

21. The computer system of claim 15, wherein the logic tree determining the one of a plurality of pre-established determinant values includes determining from dispatcher-entered input whether the patient's most prominent complaint is one of a headache, difficulty breathing and chest pain, and if so, the pre-scripted interrogation includes presenting preprogrammed inquiries for the dispatcher to ask the caller to systematically obtain additional description relating to the most prominent complaint.

22. The computer-implemented method of claim 21, wherein if the most prominent complaint of the patient is a headache, the preprogrammed inquires of the pre-scripted interrogation include asking the caller to indicate whether the headache occurred as a sudden onset of severe pain.

23. The computer system of claim 21, wherein if the most prominent complaint of the patient is difficulty breathing, the preprogrammed inquires of the pre-scripted interrogation include:
    asking the caller to identify the quality of the patient's breathing; and
    asking the caller whether the patient has had any prior flu symptoms.

24. The computer system of claim 21, wherein if the most prominent complaint of the patient is chest pain and the patient is thirty-five years old and older, the preprogrammed inquires of the pre-scripted interrogation include:
    asking the caller whether the patient is vomiting; and
    asking the caller whether the patient has chills or sweats.

25. The computer system of claim 15, wherein the preprogrammed inquires of the pre-scripted interrogation include:
asking the caller whether the patient is completely awake; and
asking the caller whether the patient is changing color.

26. The computer system of claim 15, wherein the preprogrammed inquires of the pre-scripted interrogation include inquiries asking the caller to identify whether the patient has flu symptoms including: vomiting, sweats or chills, fever, recent onset of coughing, sore throat, body aches, runny or stuffy nose, diarrhea, and headache.

27. The computer system of claim 15, the memory further comprising a pandemic diagnostic tool.

28. The computer system of claim 15, the memory further comprising a case entry protocol module.

29. A computer-readable storage medium including computer-readable instruction code for a dispatch center computer performing a method to assist a dispatcher when communicating vocally with a caller via a communication device regarding a medical emergency of a patient, the method comprising:
presenting on a dispatch center computer device a pre-scripted interrogation comprising a plurality of preprogrammed inquiries for the dispatcher to ask the caller to systematically obtain a description of the medical emergency including information concerning symptoms of the pandemic illness that the patient is manifesting, the description of the medical emergency comprising caller responses to the plurality of preprogrammed inquiries, wherein the dispatch center computer device includes a logic tree configured to determine the preprogrammed inquiries of the pre-scripted interrogation and automatically determine one of a plurality of pre-established determinant values based on dispatcher-entered input representative of caller responses to the preprogrammed inquires;

receiving dispatcher-entered input on the dispatch center computer device representative of caller responses to the preprogrammed inquiries of the pre-scripted interrogation;

assigning on the dispatch center computer device the pre-established determinant value determined by the logic tree and the pre-scripted interrogation; and generating an emergency medical dispatch response by emergency responders based on the assigned pre-established determinant value.

* * * * *